(12) United States Patent
Sones et al.

(10) Patent No.: US 6,172,748 B1
(45) Date of Patent: Jan. 9, 2001

(54) MACHINE VISION SYSTEM AND METHOD FOR NON-CONTACT CONTAINER INSPECTION

(75) Inventors: Richard Allen Sones, Cleveland Hts; Amir Reza Novini, Akron, both of OH (US)

(73) Assignee: Applied Vision, Akron, OH (US)

( * ) Notice: Under 35 U.S.C. 154(b), the term of this patent shall be extended for 0 days.

(21) Appl. No.: 09/221,372

(22) Filed: Dec. 28, 1998

(51) Int. Cl.⁷ ..................................................... G01N 21/00
(52) U.S. Cl. .................... 356/237.1; 356/239.4; 356/237.2
(58) Field of Search .............................. 356/237.1, 239.1, 356/239.4, 239.5, 239.7, 237.2, 237.3; 250/223 B

(56) References Cited

U.S. PATENT DOCUMENTS

| | | | |
|---|---|---|---|
| 4,701,612 | 10/1987 | Sturgill | 250/223 B |
| 4,786,801 | 11/1988 | Shay | 250/223 B |
| 5,461,228 | 10/1995 | Kirkman et al. | 250/223 B |
| 5,896,195 | * 4/1999 | Juvinall et al. | 356/240.1 |
| 5,900,945 | * 5/1999 | Hinata et al. | 356/428 |

FOREIGN PATENT DOCUMENTS 10-54807   2/1998   (JP) .

OTHER PUBLICATIONS

Instructions Manual for a Dual Head Gager by Emhart–Powers.
John Canny, "A Computational Approach to Edge Detection," vol. 8 (No. 6), pp. 679–698.
Optical Superresolution Using Solid–State Cameras and Digital Signal Processing.
Spencer Luster, "Telecentric Imaging: A Camera Lens, a Doublet and Thou," Light Works, pp. 192–204.

* cited by examiner

Primary Examiner—Frank G. Font
Assistant Examiner—Michael P. Stafira
(74) Attorney, Agent, or Firm—Oldham & Oldham Co., L.P.A.

(57) ABSTRACT

The invention is directed to a process of inspecting a container wherein a container is positioned at a predetermined location for inspection. At least a portion of the container is illuminated over a defined finish surface, which can relate to various complete surfaces of the container design. Illuminating light is captured from an area corresponding to the defined finish surface without physical manipulation of the container. Thereafter, it is determined whether the defined finish surface of the container is within predetermined tolerances, which then can be used for quality control or other purposes. An apparatus in accordance with the invention preferably has a source of illuminating light to direct light over defined finish surface of the container, and a light sensor to capture light from an area corresponding to at least the defined finish surface. The light sensor provides image information relating to the defined finish surface, and a processor allows determination of whether the defined finish surface is within the predetermined tolerance.

51 Claims, 10 Drawing Sheets

MACHINE VISION SYSTEM AND METHOD FOR NON-CONTACT CONTAINER INSPECTION

TECHNICAL FIELD

The invention relates generally to a container inspection apparatus and process which allows for non-contact inspection of containers, and particularly for inspection of defined surfaces associated with the container as well as dimensional characteristics thereof, including but not limited to dip, saddle, out-of-level, container height and plug gage inspection.

BACKGROUND OF THE INVENTION

Containers such as clear or translucent glass bottles are manufactured and filled in an in-line process, and thereafter are capped or sealed to enclose and protect the contents thereof. In this process, it is important that the finish surface or sealing surface of the container be free of defects which would affect proper sealing of the container or cause other problems. Other dimensional characteristics of the container must also be consistent with the sealing device such as a cap or lid, as well as the filling and capping equipment used in the in-line process. The problems associated with an improper container sealing surface or other dimensional flaws should be apparent, such as leaking of the container after the automated filling and capping process, which could include leakage of the liquid contents and/or any gas such as from carbonated liquids. Errors in finish or container dimensions may also result in damage to the filling and capping equipment, or can result in breakage of the container itself or improper operation of the filling and capping process.

An ideal container has a flat (planar) sealing or finish surface. A dip or saddle is an irregularity in the sealing surface which may prevent the container from sealing properly when a cap or lid is applied. A dip is a single localized depression or anomaly in the sealing surface, while a saddle is a saddle-shaped, or more global undulation of the sealing surface. Containers which have dip or saddle defects beyond a certain degree of severity must be rejected to avoid the above problems.

Similarly, an ideal container has a level (horizontal) sealing or finish surface. An out-of-level (tilted) sealing surface may prevent the container from sealing properly when a cap or lid is applied. Containers which are too far out-of-level must also be rejected.

The ideal container also has a smooth circular opening (bore) with a characteristic diameter. A plug (or choked neck) flaw is an irregularity in the bore or a bore having an incorrect diameter, typically a localized or global narrowing of the bore. A plugged bore can cause problems when a glass container is filled, since the filling tube which is inserted into the container may collide with the plug and break the bottle. Or, if the bore diameter is incorrect, a cork or other closing device (such as in a wine bottle) may not fit properly. Containers with opening diameters which are too small or too large, or with bores which are too non-circular, must be rejected.

All containers of the same type should have the same height (i.e., distance from the container base to its sealing surface). Containers which are too tall or too short must be rejected, as they may not be compatible with the filling or sealing equipment. Those defects (dip-saddle, out-of-level, plug and incorrect height) commonly arise during the molding process in the manufacture of glass or other containers. Mechanical inspection systems to detect these flaws have been developed and used in the glass container manufacturing industry with limited success. Further, known inspection systems generally do not provide for inspection of each of the various defects which can occur.

A known dip-saddle inspection system operates by pressing a gasketed nozzle against the container sealing surface and pressurizing the container with air. If the container has any dip or saddle defects, then the gasket does not completely seal the sealing surface and the pressurized air leaks out. The inspection system detects the reduced pressure due to leakage and rejects containers with excessive leakage.

Out-of-level inspection has also been performed by the same mechanical assembly which performs dip-saddle inspection. The gasketed nozzle which is pressed against the container sealing surface is configured so that it can swivel slightly, to conform to an out-of-level sealing surface. However, the nozzle can only swivel through a small angle $\theta$ from horizontal (two or three degrees, typically). Sealing surfaces which are more out-of-level than $\theta$ will not seal against the gasket and will fail the pressure test.

Plug inspection has been performed by inserting a cylindrical rod (plunger) into the bore of each container. The diameter of the plunger is chosen to be as large as the largest fill tube which will be used during the filling operation of the given container. If the container is plugged the plunger collides with the plug and resists complete insertion into the bore. This resistance is detected by the inspection system, so that plugged containers can be rejected.

Container height inspection has been performed by the same mechanical assembly which performs plug inspection. A "shoulder" is added to the plunger at an appropriate position and the plunger is driven down until it is stopped by the resistance of the shoulder against the container sealing surface. Adjustable limit switches are coordinated with the plunger assembly so as to identify containers which are too tall or too short.

The primary disadvantage of these mechanical inspection systems is that they are slow. The containers are typically moving down a conveyor during the inspection process, and it is mechanically complex to press a gasketed nozzle against each container sealing surface as it moves along the conveyor and as a separate step insert a plunger into the moving containers. Typical mechanical inspection systems (such as the Emhart Powers Dual Head Gager) have a throughput limit of about 200 containers per minute, while container manufacturers would prefer to sustain rates of 800 containers per minute or more.

Another disadvantage of mechanical plug gaging is that the plunger will sometimes collide with and dislodge a small glass fragment protruding from the container bore wall (called stuck glass), and this fragment will fall to the bottom of the container and stay there. If the stuck glass is fragile it may not cause sufficient resistance to the plunger to trigger rejection of the container. The presence of glass fragments at the bottom of food or beverage containers is of obvious concern. It would be desirable to provide an inspection system which not only would alleviate this problem but also would detect the presence of stuck glass.

Another disadvantage of mechanical dip-saddle gaging is that the pressure leakage technique cannot distinguish between dip and saddle defects. The leakage area of a deep narrow dip may be identical to that of a shallow saddle, so the mechanical gager sees them as identical defects. From the standpoint of manufacturing the containers, however, it is desirable to be able to distinguish these two types of defects. A dip may be harder to seal with a cap or lid than a saddle, so that the manufacturer may wish to accept saddles while rejecting dips. Additionally, the production process errors which produce dips may be different than those which produce saddles, so that distinguishing between dips and saddles may be useful for process monitoring and control.

To potentially avoid various of the problems associated with the mechanical inspection systems, there have been attempts at optical inspection techniques for certain of the container defects desired to be rejected. Such techniques have not been entirely successful as only certain of the defects desired to be found can be detected by the systems. Known optical techniques for dip-saddle gaging typically require continuous and complete rotation of the container to acquire data for the entire container sealing surface as an example, which may even be slower than the mechanical systems and are therefore ineffective. There remains the need for a container inspection system which allows a great deal of flexibility in detecting various flaws or defects in containers reliably, and as an in-line process which allows desired operating speeds to be achieved.

SUMMARY OF THE INVENTION

Based upon the foregoing, it is an object of the invention to provide a machine vision process and apparatus for inspection of containers which avoids the disadvantages of the prior art and allows accurate and reliable inspection of various container features without requiring physical manipulation of the container except that imparted to it by the container transport mechanism.

In general, the invention is directed to a process of inspecting a container which comprises the steps of positioning a container to be inspected at a predetermined location. At least a portion of the container is illuminated over a defined finish surface, which as will be described hereafter, can relate to various complete surfaces of the container design. Illuminating light is captured from an area corresponding to the defined finish surface without physical manipulation of the container. Thereafter, it is determined whether the defined finish surface of the container is within predetermined tolerances, which then can be used for quality control or other purposes. An apparatus in accordance with the invention comprises a source of illuminating light to direct light over a defined finish surface of the container, and a light sensor to capture light from an area corresponding to at least the defined finish surface. The light sensor provides image information relating to the defined finish surface, and a processor allows determination of whether the defined finish surface is within the predetermined tolerance.

The process and apparatus according to the invention provides in the preferred embodiment a machine vision approach to the inspection of dip-saddle defects, container out-of-level defects, plug defects, as well as disconformities such as incorrect height dimensions, wall thickness dimensions, check inspections or internal crack defects, stuck glass defects, as well as possibly thread inspections for a threaded container. The ability to inspect at least two of these defects simultaneously, and preferably more of such defects, provides the ability to monitor container quality in a non-contact system. In the preferred apparatus, the machine vision system has no moving parts, and is thus not subject to mechanical wear or failure, and allows inspection of containers at significantly higher operating speeds as an in-line inspection process in container manufacturing. Also in the preferred embodiment, the machine vision system may allow distinguishable detection between dip and saddle defects in the container sealing surface to allow enhanced operator process control in the manufacture of containers. The machine vision system of the invention can also provide out-of-level and height gaging for every container, allowing trends of such defects to be detected before they lead to containers which must be rejected as being out of tolerance parameters, which prior art system simply could not provide. A machine vision (non-contact) plug gage will not dislodge stuck glass and may detect such defects.

BRIEF DESCRIPTION OF THE DRAWINGS

The objects and advantages of the invention will become apparent upon a further reading of the detailed description of the preferred embodiments in conjunction with the figures, wherein.

DETAILED DESCRIPTION OF THE PREFERRED EMBODIMENTS

Figure 1:
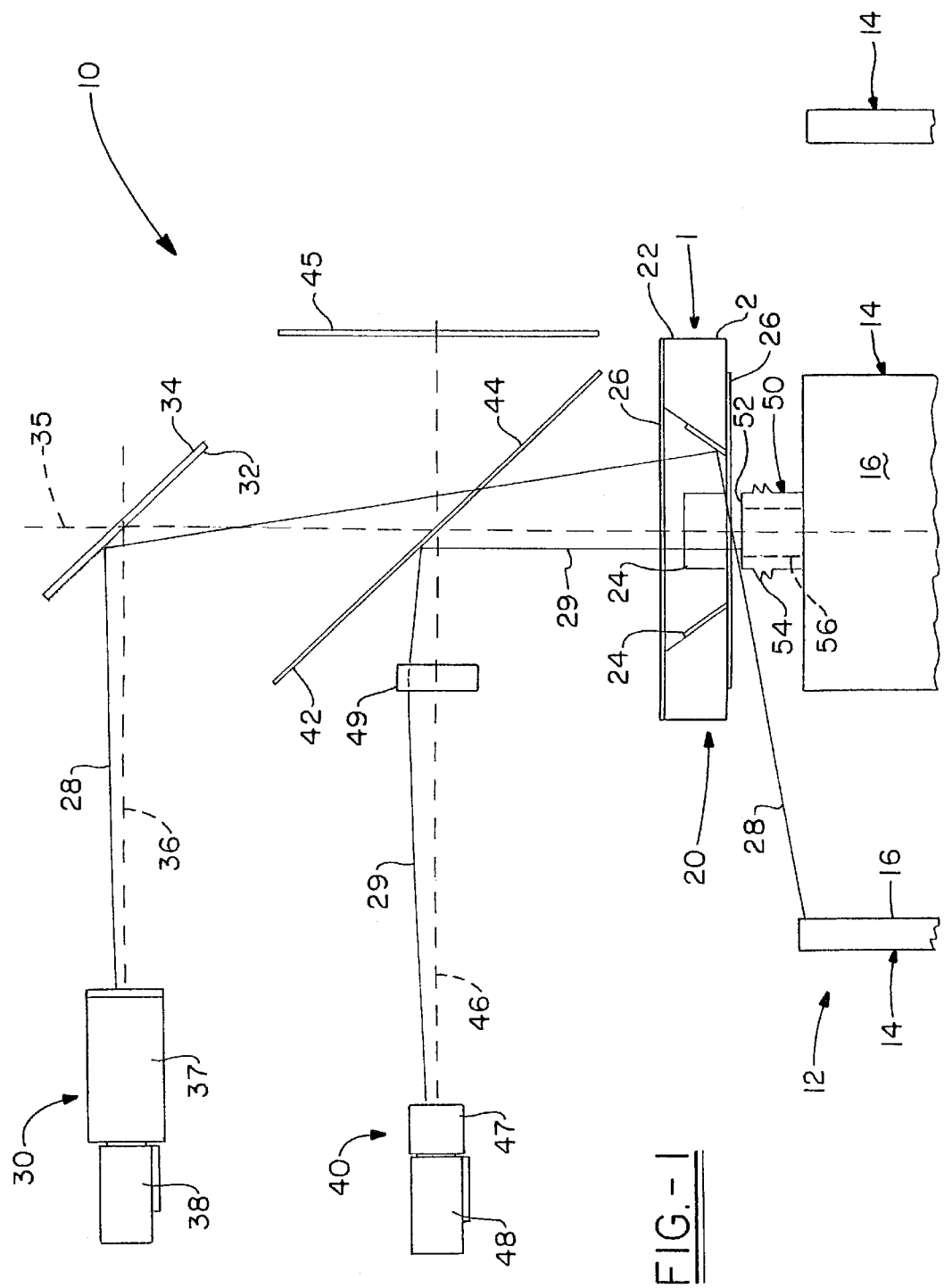
FIG. 1 is a generally schematic view of a preferred machine vision apparatus according to the invention.
Figure 2:
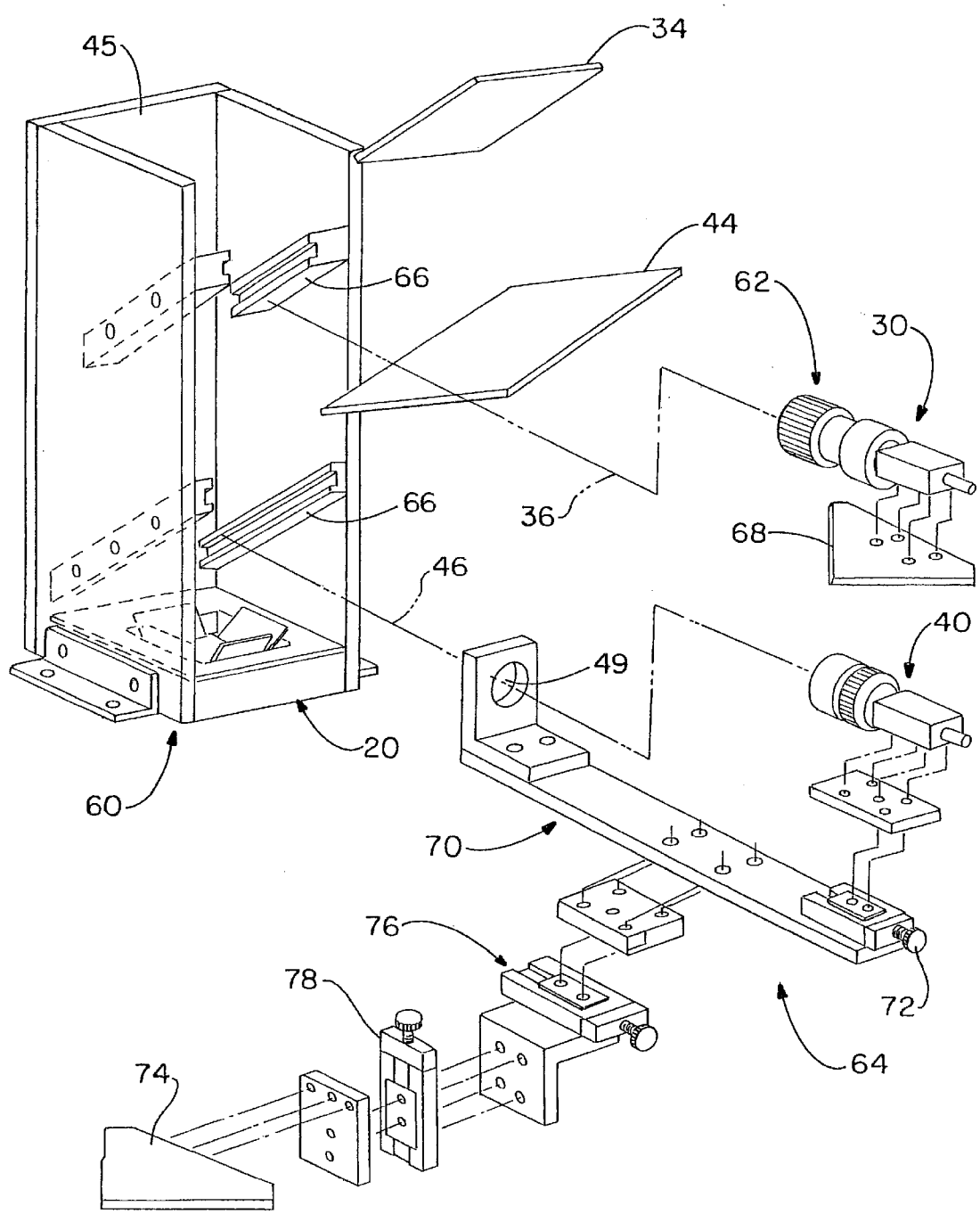
FIG. 2 is an exploded perspective view of an embodiment of the apparatus as shown in FIG. 1.

Turning now to FIG. 1, a machine vision apparatus generally designated 10, allows inspection of a container 50 which is positioned at a predetermined location for inspection. As it is intended the invention will allow inspection of containers in a manufacturing process as an in-line operation, container 50 will typically be moving at high speed in a processing line, where containers can be automatically filled and sealed if the characteristics of the container 50 are consistent with predetermined tolerances.

Container 50 may be a glass bottle or other container having an open top which must be sealed subsequent to filling of the container. The container 50 therefore includes a sealing surface 52, which must have characteristics within defined tolerances to allow proper sealing of the container. Various defects to be detected by the process and apparatus of the present invention relate to the sealing surface 52, and it is one surface which will be described herein as a "defined finish surface". The container 50 may also include one or more threads 54, used to secure a lid in association with the open top and over sealing surface 52. The outside diameter associated with portions of threads 54 may be inspected for disconformities, and may comprise a defined finish surface according to the invention. The threads 54 must be formed in accordance with predetermined tolerances to allow proper fitting of a cap in association therewith. The open top in many cases will be a circular bore 56, which is designed to be of a predetermined diameter to allow access of automatic filling equipment. A substantially circular surface comprised of a diameter of the bore 56 may be a defined finish surface according to the invention, to allow inspection of the bore for conformance to predetermined tolerances.

In the preferred embodiment of the invention, the machine vision system 10 provides inspection of dip-saddle, out-of-level, plug and height inspection for the container 50, without physical contact with the container 50, and using no moving parts (except for the moving container itself via the container transport mechanism). In this manner, the machine vision system 10 allows significantly faster operation than a mechanical or other optical inspection system, and requires no physical manipulation of the container 50. In the preferred embodiment, throughput of 800 or more containers 50 per minute can be readily achieved, allowing significantly improved filling and capping of containers 50 in a production line. Other irregularities with the container 50 may also be detected using system 10, including wall thickness at the area of bore 56, stuck glass inspection as well as other parameters as will become apparent. Each of the inspections which may be performed by system 10 are preferably carried out simultaneously, but also could be performed independently if desired.

The machine vision system 10 in the preferred embodiment includes an illumination system generally designated 12, which may include a plurality of illumination sources 14. In the preferred form, illumination sources 14 may be comprised of a large number of high intensity LED components, directing light through a diffusing front panel 16 to provide high intensity, substantially uniform illuminating light from predetermined locations surrounding container 50. It should be recognized that a number of configurations for positioning illuminating lights 14 about container 50 to provide proper illuminating light for a particular container configuration are within the scope of the invention. Positioned above container 50 is an optical assembly 20. It should be noted that optical assembly 20 in its relative position to container 50 will not inhibit travel of container 50 in a production line. In the preferred embodiment, the optical assembly 20 comprises a multi-mirror assembly mounted within a housing 22. The position of housing 22 may be selectively varied for particular container configurations to allow proper inspection of defined finish surfaces associated with the container 50. A plurality of reflecting mirrors 24 are positioned in housing 22 at predetermined locations relative to container 50, and disposed at a predetermined angle. In the preferred form, protective windows 26 may be positioned above and below the mirror assemblies 24 to protect mirrors 24 from dust and abrasion. It should be recognized that windows 26 are not necessary for providing optical characteristics in the assembly 20, and may be dispensed with.

Light from sources 14 provide backlighting from positions surrounding the defined finished surfaces of interest of container 50, with an illustrative optical ray 28 originating at a light source 14. The optical ray 28 is shown to graze the top sealing surface 52 of container 50 for inspection of this surface in accordance with a dip-saddle inspection method. The optical ray 28 is then incident upon a mirror 24 in assembly 20, and is reflected to at least a first light sensing system generally designated 30. For dip-saddle inspection method according to the invention, the light sources 14 are positioned to provide backlighting against the sealing surface 52 from positions surrounding container 50, such that optical rays 28 will be incident upon light sensing system 30 from substantially the entire sealing surface 52, corresponding to a defined finish surface to be inspected. For dip-saddle inspection, the container 50 will be positioned such that the central axis through the open top of container 50 is substantially coincident with the primary optical axis 35 of the machine vision system 10. In order to minimize the dimensions of the machine vision system 10, a reflective surface 32 of first-surface mirror 34 folds the primary optical axis 35 onto a secondary optical axis 36. The light sensing system 30 may comprise a zoom lens 37 mounted to an imaging camera 38, both being aligned along the secondary optical axis 36. In this preferred configuration, the dip-saddle inspection allows viewing of the sealing surface 52 of container 50 from a substantially horizontal vantage point via mirrors 24 and 34. The zoom lens 37 is provided to focus light incident upon it from the sources 14 about the sealing surface 52 onto a CCD sensing system associated with the imaging camera 38. Alternatively, a condensing lens system could be used to focus light on camera 38. Any refractive effects of windows 26 associated with the optical assembly 20 are accounted for, or are negligible.

Also in the preferred embodiment, other of the defined finish surfaces of container 50 may be simultaneously inspected. A plug gage inspection using light sensing system 40 allows defined finish surfaces comprising diameters of bore 56 to be inspected for conformity to predetermined tolerances. Plug gage inspection also allows for inspection of stuck glass defects within the bore 56. Alternatively, the diameters of threads 54 may be inspected using a second light sensing system 40. In the preferred embodiment, a light source 14 is positioned below container 50 to provide backlighting for these defined finish surfaces, with one illustrative optical ray 29 shown to graze the inside surface of bore 56 as an example. A reflective surface 42 associated with a beam-splitting mirror 44 folds primary optical axis 35 onto a tertiary optical axis 46. The light sensing system 40 may comprise a focusing lens 47 associated with an imaging camera 48, with both lens 47 and imaging camera 48 aligned along the tertiary optical axis 46. Positioned along tertiary optical axis 46 may also be provided a condensing lens 49, disposed between lens 47 and beam splitting mirror 44. In the preferred embodiment, lens 49 is positioned at the back focus with respect to camera lens 47 and at a distance along the optical axes 35 and 46 to the container 50 being substantially equal to the focal length of lens 49. As the machine vision system 10 is designed in the preferred embodiment to be used in a production environment, a baffle 45 may be positioned to inhibit ambient light from being transmitted through the beam splitting mirror 44 to the camera 48 along optical axis 46, or from folding mirror 34 to the camera 38.

FIGS. 2–7 illustrate an embodiment of the machine vision system 10 as described with reference to FIG. 1 for use in a container production environment. The elements of the system 10 may be positioned with respect to one another in a housing 60, with each of the components provided in a sub-assembly. Three principal sub-assemblies include optical assembly 20, dip-saddle imaging system 62 and bore imaging system 64. The folding mirror 34 and beam-splitting mirror 44 are mounted with brackets 66 for precise positioning. The dip-saddle sub-assembly 62 is mounted via a bracket 68 in proper position along optical axis 36 provided by mirror 34. Similarly, the bore imaging system 40 is mounted on a supporting bracket 70, and particularly may be supported on an adjustment mechanism 72 to allow selective adjustment of the position thereof with respect to other optical components. Also mounted on bracket 70 may be the condensing lens 49, which also may be adjustably positioned relative to bracket 70 if desired. The imaging system 40 and lens 49 are then mounted on a supporting bracket 74 via adjustment mechanisms 76 and 78 which allow selective adjustment of the entire sub-assembly 64 with respect to housing 60. In this manner, each of the optical or imaging components of the machine vision system 10 are individually and selectively adjustable to ensure proper positioning for imaging of various defined finish surfaces associated with a container 50 to be inspected.

Figure 3:
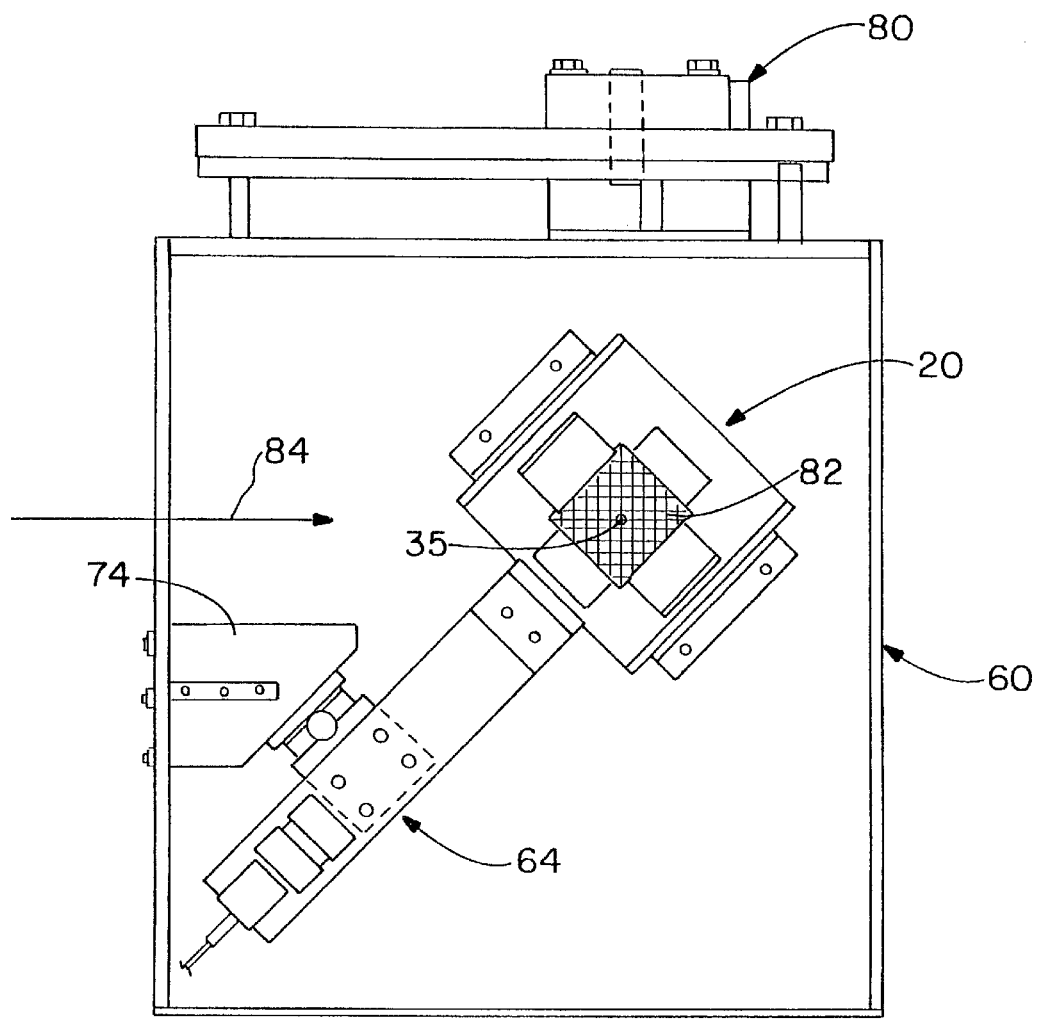
FIG. 3 is a top view showing the mounting of a first imaging system associated with the apparatus as shown in FIG. 2.
Figure 4:
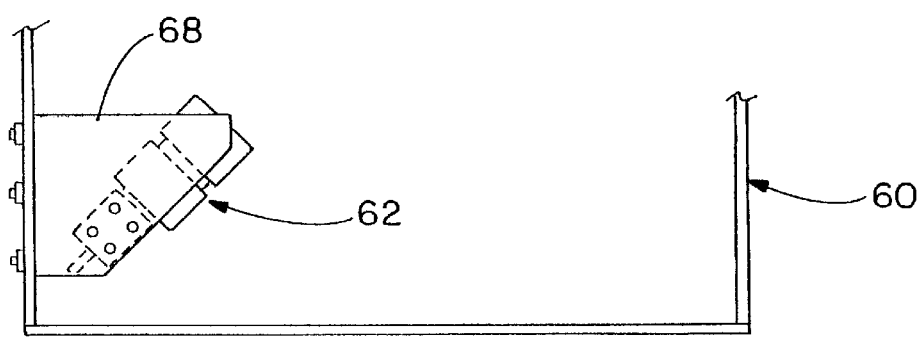
FIG. 4 is a partial top view of a second imaging system associated with the apparatus as shown in FIG. 2.

FIGS. 3 and 4 show top views of the sub-assemblies 20, 62 and 64 as mounted within housing 60. The entire housing 60 may itself be supported on a support structure 80 in an adjustable manner, with supporting structure 80 being associated with a container conveyor system (not shown) or positioned adjacent thereto. Alternatively, the support structure 80 may allow portability of the entire machine vision system 10 to be selectively positioned at any location along a container production line as an in-line inspection station. In the preferred embodiment, the housing 60 fully encloses the optical and imaging components of the machine vision system 10, with a bottom opening 82 provided to position optical system 20 above containers to be inspected. In the desired configuration, the optical system 20 has the bottom window 26 disposed through opening 82 so as to be recessed into the base of the enclosure 60 with the bottom surface of window 26 being substantially flush with the bottom surface of the enclosure 60. Containers will travel along the line 84 toward opening 82, and when positioned as desired relative to optical axis 35, will allow inspection of predetermined defined finish surfaces of the container 50 which are preferably simultaneously inspected. Although providing a great amount of versatility, the machine vision system 10 also occupies little space, and allows for selective adjustment or removal of the sub-assemblies 20, 62 and 64 if desired.

Figure 5:
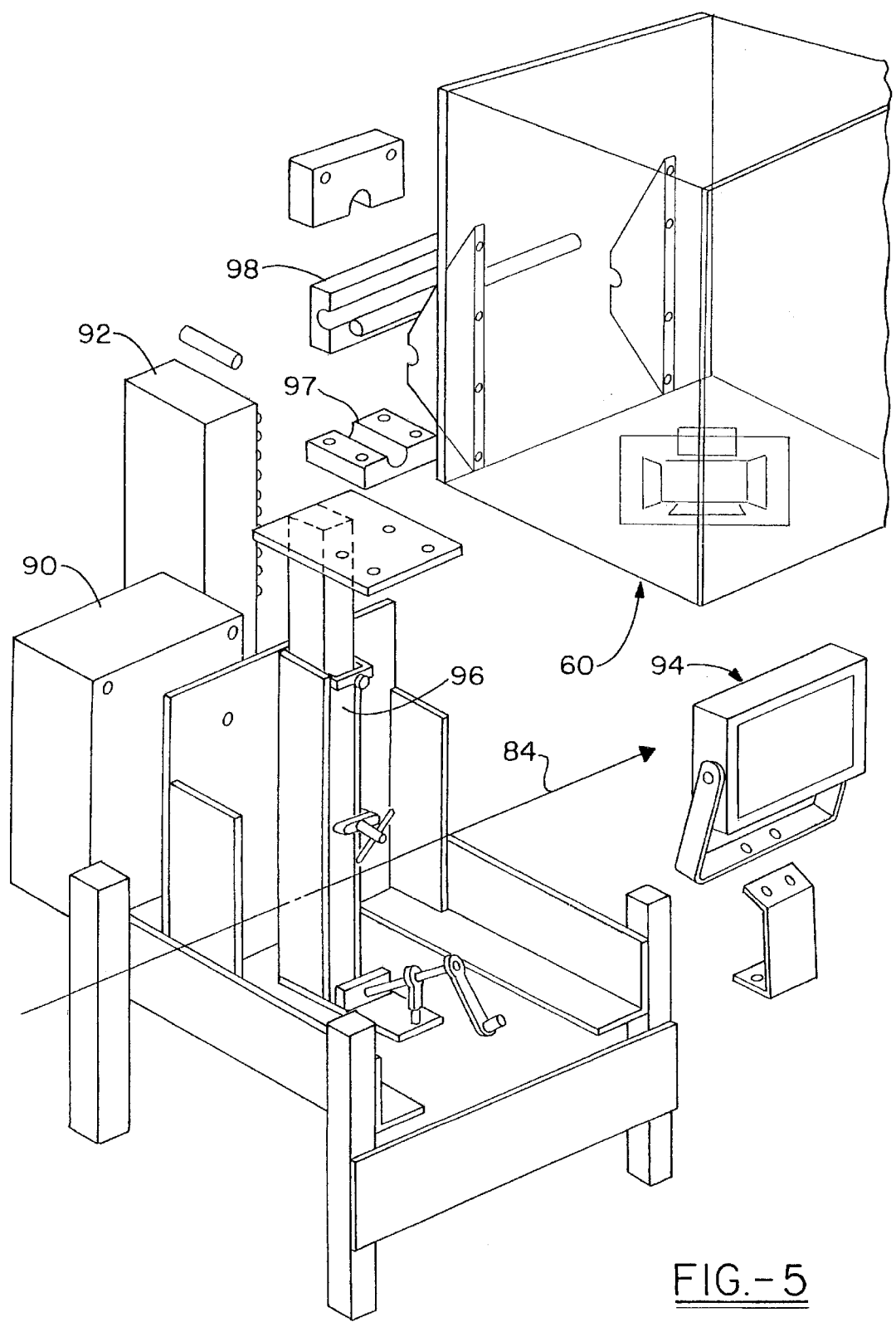
FIG. 5 is an exploded perspective view of the machine vision system as shown in FIG. 2 in an embodiment for use as an in-line inspection system for containers moving along a processing line.

FIG. 5 shows a possible supporting structure for the machine vision system 10 in accordance with the preferred embodiment, which again will allow for selective positioning of system 10 in a desired location relative to containers to be inspected traveling along a path 84. The supporting structure 80 may also carry a processing system 90 to which are fed image signals from the sensing systems 30 and 40 for analysis as will be further described. In the desired configuration, the systems 30 and 40 are CCD imaging systems which provide video signals to the processing system 90. The processing system 90 may be housed in an enclosure which is cooled by an air conditioner 92. A user interface 94 may be coupled to the processing system 90, for control of the machine vision system 10, with interface 94 being any suitable interface, such as an LCD touch-screen interface as an example. The housing 60 may be supported on an adjustable-height column 96 via a movable platform arrangement, with the enclosure 60 also being movable via adjustment mechanisms 97 and 98. It should be seen that this supporting arrangement allows positioning of the machine vision system 10 in the proper location relative to the path of travel 84 of containers to be inspected, without inhibiting the path of travel in any manner. As the machine vision system 10 is designed to inspect containers in a non-contact manner, operating speeds of the processing line are unaffected.

Figure 6:
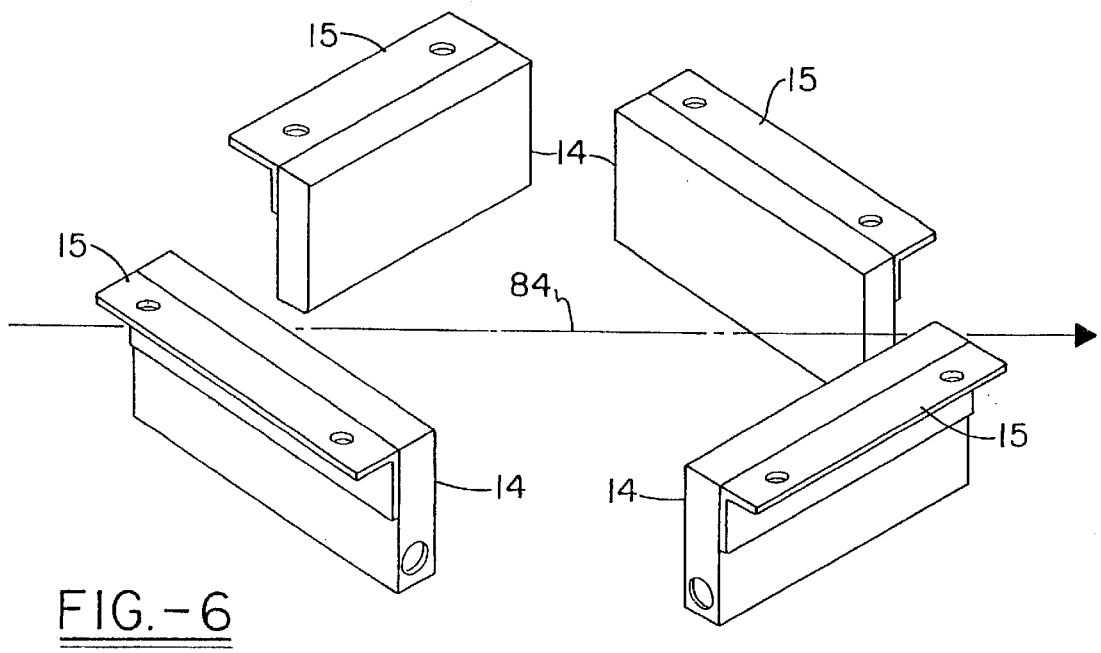
FIG. 6 is a partial perspective view showing a preferred illumination system according to the invention.
Figure 7:
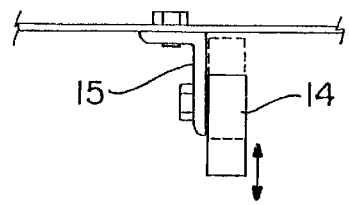
FIG. 7 is a side view of an illuminating light source indicating adjustability of its position for inspection of different containers.

FIG. 6 shows an example of the illuminating light configuration for inspection of various defined finish surfaces associated with the container, again without affecting the travel path of containers to be inspected. In one preferred embodiment, the backlighting for dip-saddle inspection positions illuminating light sources 14 at angular positions relative to the travel path 84. The light sources 14 may be mounted on the underside of the enclosure 60 about opening 82 to allow access of a container while providing substantially uniform illuminating light from positions which substantially surround a container positioned at axis 35. In the preferred embodiment, a limit switch or the like may detect the presence of a container along the travel path 84, and the illuminating light sources 14 may be strobed by means of the control system 90 at the instant the container is substantially aligned with the optical axis 35. In this manner, a discrete image of the defined finish surfaces of interest is generated, from which it may be determined whether flaws exist in the defined finish surfaces. As shown in FIG. 7, the individual light sources 14 are also preferably adjustable in position, such as by vertical and horizontal adjustment of the light source relative to a supporting bracket 15.

As mentioned with respect to the preferred embodiment, it would be desirable to simultaneously inspect various defined finish surfaces of the container using machine vision system 10. In the preferred configuration, the optical assembly 20 provides for inspection of the sealing surface 52, and includes four reflecting mirrors 24, each of which reflects a silhouetted view of the sealing surface 52 of container 50. Each of the views provided by mirrors 24 in optical assembly 20 is directed to imaging system 30 as an example. The image generated may then be analyzed for defects outside of predetermined tolerances associated with the defined finish surfaces for acceptance or rejection of containers in a manufacturing operation.

Figure 8:
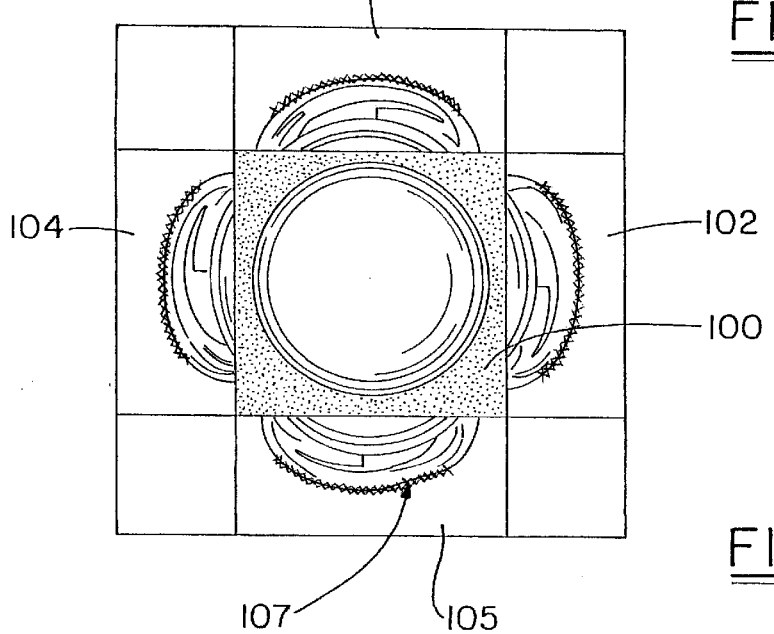
FIGS. 8–9 are images of various container defined finish surfaces which are desired to be monitored for determination of required tolerances in the container.

In the embodiment of the machine vision system 10 as shown, the images produced by the optical system 20 in association with system 30 are shown in FIG. 8. The image contains five image regions: a central region 100 which provides a direct view of the opening of container 50, such as a glass fruit juice bottle, and peripheral regions 102, 103, 104 and 105 which are reflections or silhouetted images of the bottle sealing surface 52 (a defined finish surface) in mirrors 24. The peripheral image regions may be used to perform inspection of the sealing surface, referred to as the dip-saddle inspection, and the central image region may provide possible detection of check flaws in the bottle opening or is not used. The image provides a top view of the sealing surface 52, but in silhouette, preferably from a shallow viewing angle to reveal defects. The multi-mirror assembly 20 provides a number of images which are designed to overlap to some extent, to thereby image the entire defined finish surface simultaneously. In this embodiment, region 102 shows a silhouette of the left portion of surface 52; region 103 shows a silhouette of the bottom portion of surface 52; region 104 shows a silhouette of the right portion of surface 52; and region 105 shows a silhouette of the top portion of surface 52. Distortion 107 in the smooth outline of the bottle finish corresponds to a dip defect in surface 52.

The central region 100 is seen to show an image of the sealing surface 52 and bore of the container opening. Although a blacklight positioned beneath container 50 would illuminate the central region of image 100, the opening of the container 50 would still appear similar to that shown in FIG. 8. Possible occurrences of check defects or small fractures within the area of the container opening may be detected within this region by noting atypical reflections within this region corresponding to the opening neck of container 50.

Figure 9:
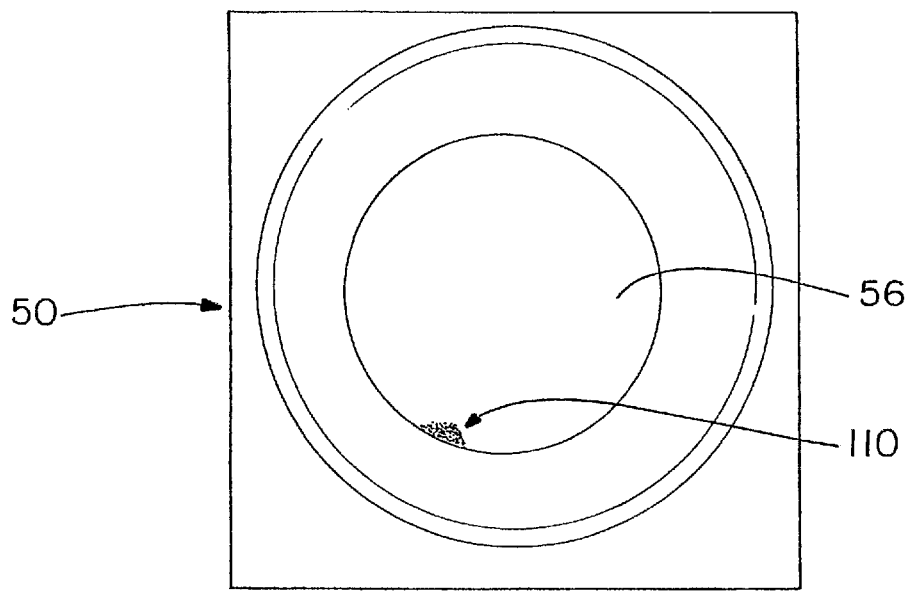

Simultaneously, the imaging system 40 acquires an image of the container 50 as shown in FIG. 9. This image is of a glass beverage bottle, with a bore 56 and stuck-glass defect 110. The bore region is bright because of a blacklight located below the container 50, and the fact that the container bottom is transparent or translucent. The optical system including lens 49 and camera lens 47 forms the image which allows bore tolerances to be inspected along with defects such as stuck glass 110 to be detected. The wall thickness characteristics may be analyzed, and again the detection of check defects may be provided.

Figure 10:
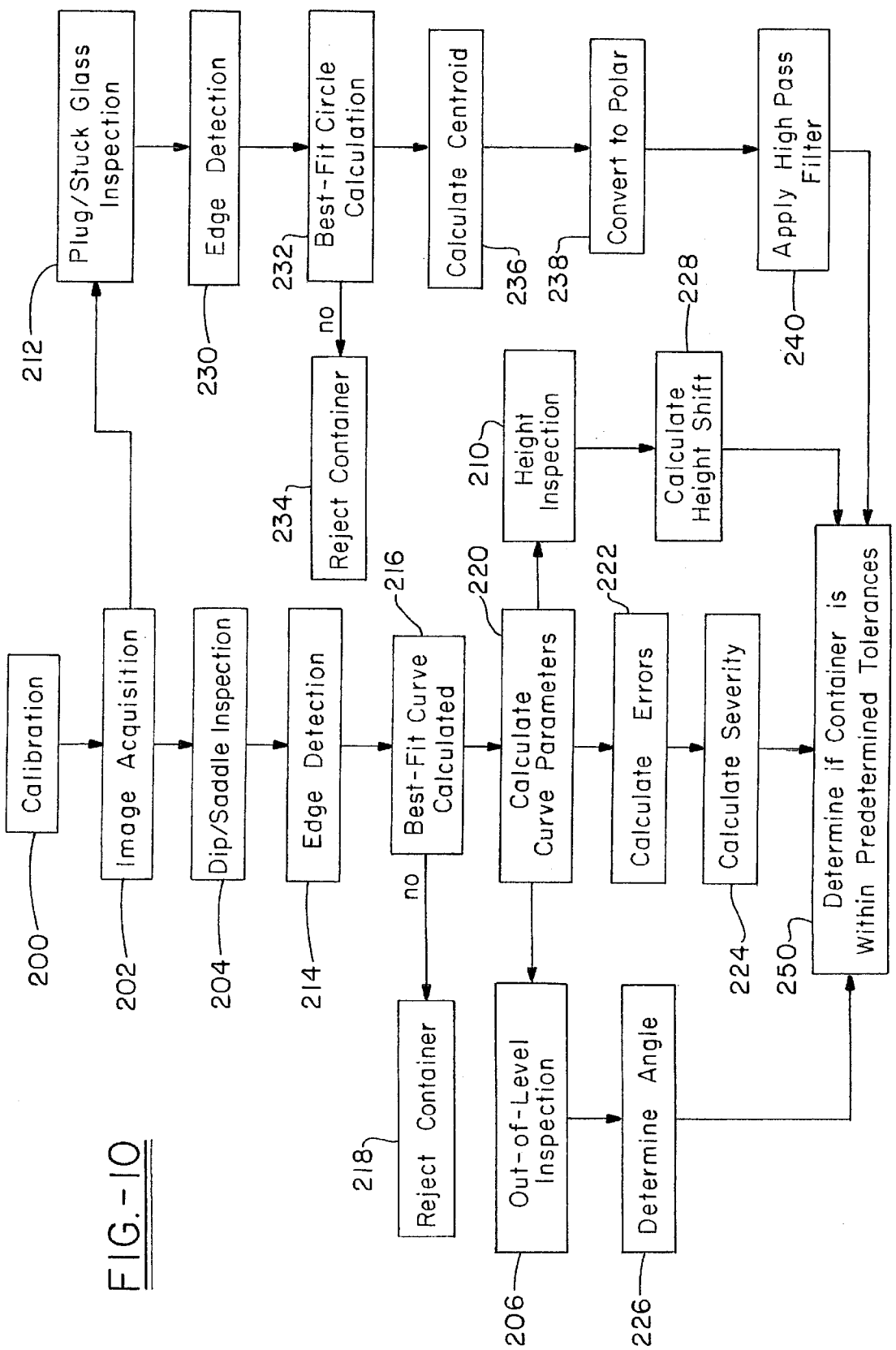
FIG. 10 is a flow diagram of the processes of the invention according to a preferred embodiment.

Turning now to FIG. 10, the process of evaluating various defined finish surfaces in an in-line process according to a preferred embodiment of the invention will be described. Based upon a particular container configuration to be inspected according to the process of the invention, and using an apparatus such as described herein, the apparatus may first require calibration at 200 for a particular container. The step of calibrating the system may be simply positioning a known container which has defined finish surfaces within predetermined tolerances at a position corresponding to the optical axis of the optical system of the apparatus. This step may utilize the conveyor on which containers to be inspected will travel, or may be positioned manually. Upon the conveyor, a limit switch will be activated and a part-present signal generated, indicating the container is positioned correctly for inspection, and the illumination system may be strobed to acquire an image of the defined finish surface of interest, such as the sealing surface. Using the sealing surface as an example, the optical system will form an image of a smooth polynomial curve, which for a circular sealing surface about a container opening will be elliptical in accordance with the preferred embodiment. Using sub-pixel edge detection to extract the silhouette of the sealing surface profile from the plurality of reflecting mirrors in the optical system allows a smooth polynomial curve to be formed for the entire sealing surface as desired. Upon application of linear regression as described a best-fit ellipse for each of the four sealing surface profiles is determined. Each of the best-fit ellipses will then form the basis for analysis of containers in the in-line inspection process. For each ellipse, the semi-major and semi-minor radii can then be determined along with the location of its center point, which then allows calculation of the calibration viewing angle for each of the four mirrors.

Thereafter, the step of image acquisition can be performed at step 202 for containers to be inspected traveling on the container transport conveyor. The control system waits for the part-present activation signal indicating the container is properly positioned, and simultaneously will control the system to strobe the illuminating lights. In the preferred embodiment, the backlights for the dip-saddle inspection and for the plug gage inspection are strobed simultaneously to acquire a plurality of images for each of the entire defined finish surfaces of interest and the calculation of each of the parameters as previously described.

Once the image is acquired for each of the defined finish surfaces to be inspected, the control system can then analyze the defined finish surfaces, and particularly the sealing surface is analyzed for dip/saddle defects at 204, out of level defects at 206 and height inspection at 210. The defined finish surface of the plug is analyzed at 212 along with any stuck glass defects. For the dip/saddle analysis, the surface edge detection is performed at 214 for each surface profile image, and thereafter a best-fit polynomial curve is found at 216 for each. By forming images from shallow viewing angles across a circular sealing surface, the curve will be elliptical, and any best-fit curve which is not elliptical will immediately indicate a defect of significant severity, and the container is rejected at 218. Otherwise, the parameters of the best-fit ellipse are calculated at 220, including the semi-major and semi-minor radii of each surface profile image, the coordinates of its foci, and the coordinates of the center. The sealing surface profile data at 204 and the curve parameters calculated in step 220 can then be used to calculate any errors at 222 for each view of the surface profile, with the errors correlating to the distance between the actual edge of the container and the best-fit curve. Using the error data calculated, the severity of the dip and/or saddle defects are determined at 224.

The out-of-level analysis at 206 is performed by using the calibration viewing angles determined during calibration, and the semi-major and semi-minor radii determined at step 220. From these parameters, the out-of-level angle of the sealing surface is determined at 226.

The height inspection and analysis at 210 uses the calibration ellipse center data and calibration viewing angles as determined at step 200 to determine the height shift between the measured sealing surface and the calibration container at 228.

The plug surface analysis at 212 is initiated by the edge detection of the surface from the acquired image at 230. The diameter of the largest circle inscribed in the plug opening is determined at 232, and can be compared to the calibration data or a user defined threshold to determine if this surface is clearly outside acceptable container parameters at 234 and rejected. If the diameter is not outside this threshold, the centroid of the bore outline is calculated at 236, and the points comprising the bore outline are converted from rectangular to polar coordinates at 238. A user defined high pass filter may then be applied at 240.

Using the calculated values for dip and/or saddle severity at 224, the determination of the out-of-level angle at 226, the height shift at 228 and the results of applying the high pass filter to the plug surface data at 240, the determination of whether to accept or reject the container is then made at 250, by comparison of these values with user defined threshold values. Thus, as an example, if the application of the high pass filter at 240 yields filtered values of the bore outline which exceed a user-defined threshold, the container is rejected as having a stuck glass defect. Similar comparisons are made for each of the desired parameters. It should also be noted that should other parameters be of interest, such as thread inspection or check defects, these can be analyzed simultaneously. Each of these inspection procedures will be described in more detail hereafter.

Sealing Surface Inspection

Figure 11:
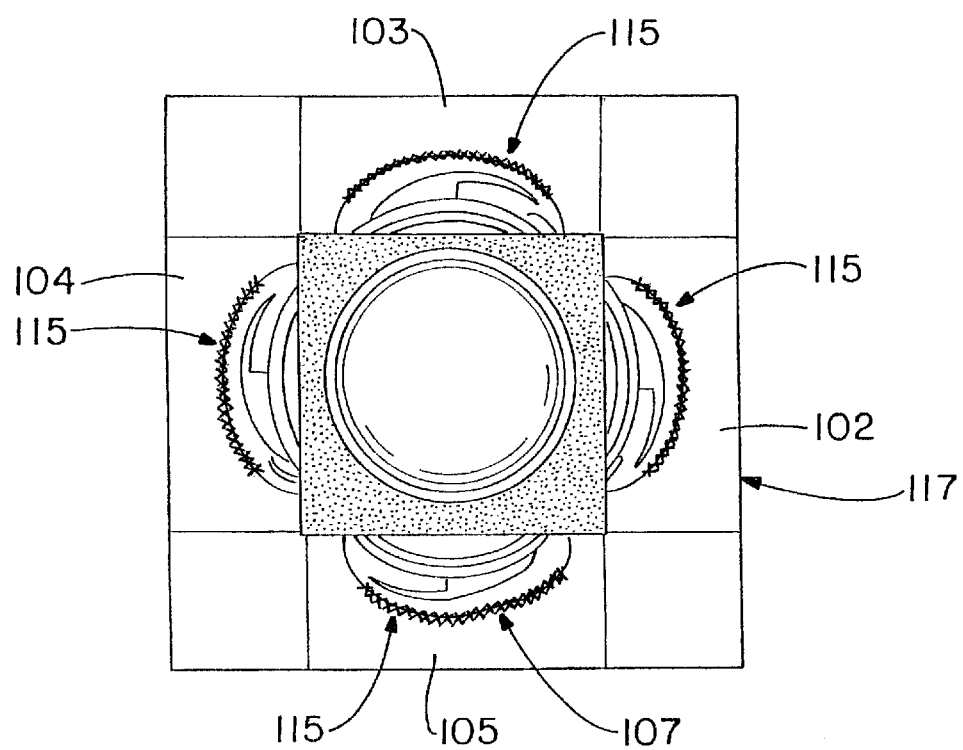
FIG. 11 is an image of a container showing detection of certain defects in defined finish surfaces of the container.

FIG. 11 is similar to FIG. 8 except that white crosses 115 have been added where silhouetted edges of the sealing surface 52 were located using processing system 90. The white rectangles indicate four "regions of interest" 117 within which the processing system 90, and more particularly an image processing sub-system, searches for edges. Edge finding algorithms (with sub-pixel resolution) are known in image processing literature (see, for example: "A Computational Approach to Edge Detection" by John Canny, IEEE Transactions on Pattern Analysis and Machine Intelligence, Vol. PAMI-8, No. 6, pp. 679–698, November 1986; "Optical Superresolution Using Solid-State Cameras and Digital Signal Processing" by Peter Seitz, Optical Engineering, Vol. 27, No. 7, pp. 535–540, July 1988), and may be used in the invention. The edge finding in region 102 may be performed by scanning from right to left along pixel rows (y coordinate) within the region of interest 117 of the image and locating the column (x coordinate, determined to sub-pixel resolution) of the first significant light-to-dark transition. A user-specified number of rows centrally located within regions 117 may be used, which governs the resolution or how much of the sealing surface 52 is "covered" by each of the four views. The set of x and y coordinates of the edge points found in region 102 defines the locus of a portion of the silhouette of the sealing surface 52. Similarly, the edge finding in region 103 may be done by scanning columns from top to bottom within the predetermined region 117; the edge finding in region 104 by scanning rows from left to right; and the edge finding in region 105 by scanning columns from bottom to top. Once these four sets of coordinates (loci of the sealing surface silhouettes) are extracted from the dip-saddle image, the image is no longer needed and may be discarded. It should be noted that the white crosses 115 indicating the edge points and white boxes 117 are used for illustrative purposes only, and during an actual inspection there is no need to display them. Indeed, it is not even necessary to display the acquired image, except as feedback to the system operator that things are working properly.

An ideal container, such as a glass container, has a smooth circular and level sealing surface 52. As shown in FIG. 11, the silhouetted portion of the sealing surface 52 provides a view of this surface from a viewing angle such that the circular surface appears as a smooth polynomial curve, which for the imaged container would be an ellipse if properly formed. The presence of a dip and/or saddle defect in sealing surface 52 will distort the elliptical shape, and can be detected to determine whether sealing surface 52 is within predetermined tolerances. As measured from the edge detection, the loci of the sealing surface silhouettes will deviate from an ellipse, and can be detected, with the severity of any deviations corresponding to the severity of the defect.

The processing system 90 will contrast the measured loci from the images with an ideal container specification relating to a specific container configuration or a user defined container. The equation of an ellipse in the xy plane may be written (see, for example, "Manual of Mathematics" by Korn and Korn, McGraw-Hill Book Company, 1967, Section 2.3)

$$a_{11}x^2 + 2a_{12}xy + a_{22}y^2 + 2a_{13}x + 2a_{23}y = 1, \quad (1)$$

where the a's are constants and the assumption is made that the ellipse does not contain the point x, y=0. The three quantities $$I = a_{11} + a_{22}, \quad (2)$$

$$D = \begin{vmatrix} a_{11} & a_{12} \\ a_{12} & a_{22} \end{vmatrix} \quad (3)$$

and $$A = \begin{vmatrix} a_{11} & a_{12} & a_{13} \\ a_{12} & a_{22} & a_{23} \\ a_{13} & a_{23} & -1 \end{vmatrix} \quad (4)$$

are invariant with respect to translation and rotation of the ellipse. (The vertical bars surrounding the matrices represent the matrix determinant.) In order for Eq. (1) to describe a real ellipse (as opposed to a hyperbola, for example) the conditions $$D > 0$$

and $$AI^{-1} < 0 \quad (5)$$

must be satisfied.

Given the set of N points $x_i$, $y_i$ ($0 \leq i < N$) corresponding to a set of measured locus points 115 (see FIG. 11), linear regression may be used to determine the values of the a's which best describe the measured points, in the sense that the sum-of-squared-errors quantity $$\chi^2 = \sum_{i=0}^{N-1} (a_{11}x_i^2 + 2a_{12}x_iy_i + a_{22}y_i^2 + 2a_{13}x_i + 2a_{23}y_i - 1)^2 \quad (6)$$

is minimized. (Linear regression is a standard tool of numerical analysis, so the algebraic details will not be given here. See, for example, "Numerical Recipes in C: The Art of Scientific Computing" by Press, Flannery, Teukolsky and Vetterling, Cambridge University Press, 1990, Section 14.3.) If conditions of Eq. (5) are not satisfied then the best-fit curve described by Eq. (1) is not an ellipse, implying that the sealing surface 52 has a severe dip or saddle and must be rejected. If the best-fit curve is an ellipse, then its major ($r_>$) and minor ($r_<$) radii, the coordinates ($X_0$, $Y_0$ and $X_1$, $Y_1$) of its foci, and the coordinates ($X_c$, $Y_c$) of its center are calculated.

Next the errors $$\epsilon_i = \sqrt{(x_i - X_0)^2 + (y_i - Y_0)^2} + \sqrt{(x_i - X_1)^2 + (y_i - Y_1)^2} - 2r_> \quad (7)$$

are calculated. The value $\epsilon_i$ represents in general how far the measured point $x_i$, $y_i$ falls from the best-fit ellipse, with the unit of distance the center-to-center pixel spacing. Equation (7) is based on the well-known property of an ellipse that the sum of the distances from a point on the ellipse to the foci is equal to the length of the major axis. Hence, $\epsilon_i = 0$ corresponds to a point on the ellipse, $\epsilon_i > 0$ corresponds to a point outside the ellipse, and $\epsilon_i < 0$ corresponds to a point inside the ellipse.

Figure 12:
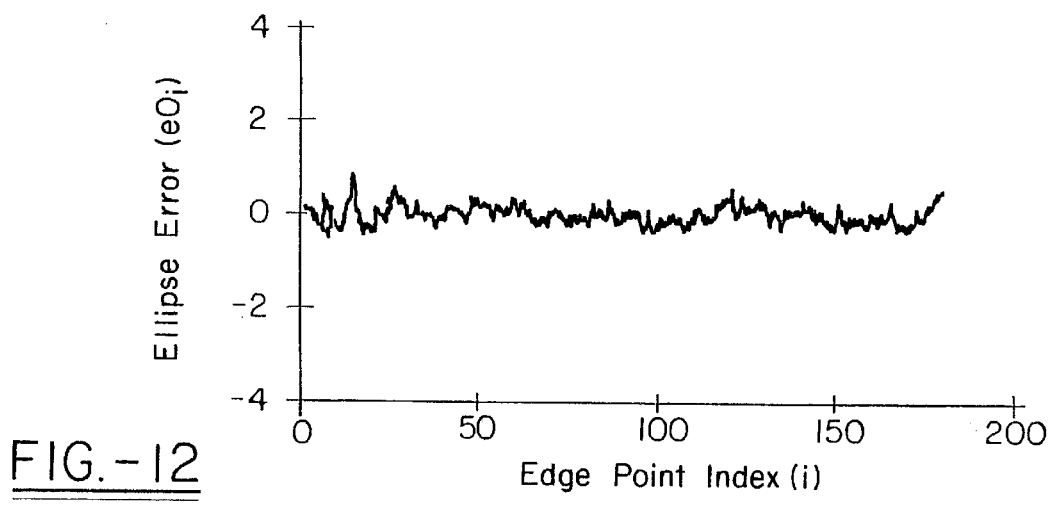
FIGS. 12–15 are graphical representations of image information relating to defined finish surfaces of a container for determination of whether the defined finish surface is within predetermined tolerances.
Figure 13:
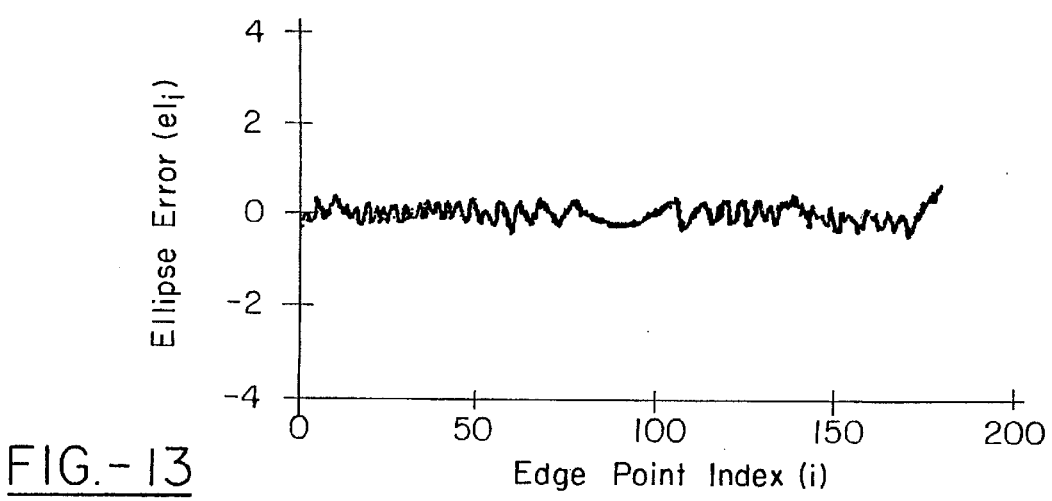
Figure 14:
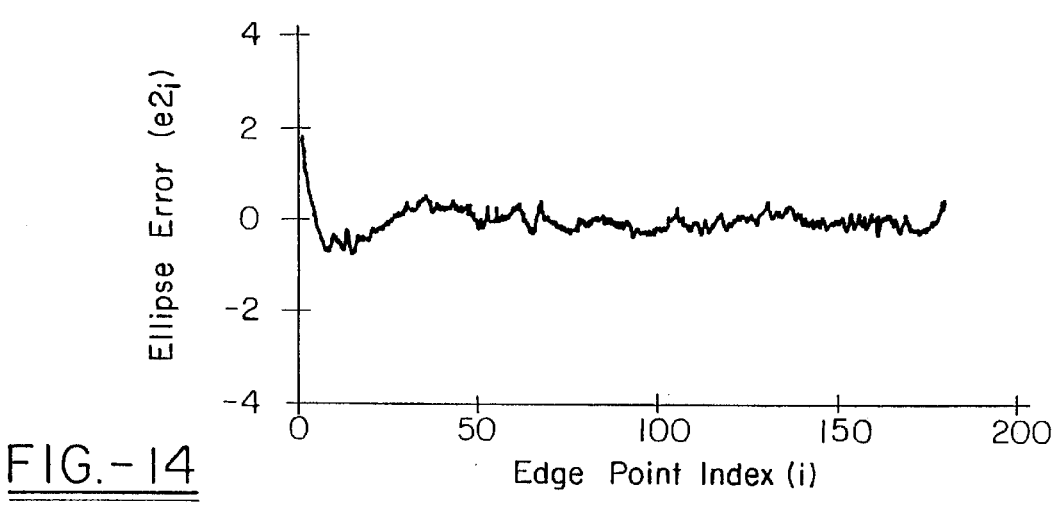
Figure 15:

Plots of $\epsilon_i$ versus i are shown in FIGS. 12–15, which correspond to the images from regions 102–105 as shown in FIG. 11. The curve fitting and error calculations were performed independently for each view. The value of i increases from top to bottom in regions 102 and 104, and from left to right in regions 103 and 105. Note that the errors measured from the edges in regions 102 and 103 as shown in FIGS. 12 and 13, are relatively small (magnitude less than one pixel) and show no consistent trend (just random noise), while the errors from region 105 in FIG. 15 are relatively large and show a distinct oscillatory behavior. The errors from region 104 in FIG. 14 are mostly small and trend-free, except at the extreme left side of the plot where a large oscillatory "spike" is apparent. These results indicate that there is a localized (i.e., dip) defect in the portion of the sealing surface seen in regions 104 and 105, with the bulk of the defect in 105. This is consistent with the appearance of the defect as shown in images of FIGS. 8 and 11.

Let $\epsilon_i^{(j)}$ denote the errors calculated for mirror j(j=0,1,2,3 relating to the views as shown in each mirror of mirrors 102–105 as shown in the preferred embodiment of FIG. 8). In order to automate the dip-saddle inspection, an algorithm which inputs the $\epsilon_i^{(j)}$ and outputs a measure of the severity of dip and saddle is desired. The following general procedure has been found effective. Let $$\epsilon^{(j)} = f(\epsilon_i^{(j)}) \tag{8}$$

be a single-number measure of the severity of the dip-saddle flaw corresponding to mirror j, where $f$ is a function which is zero if the errors are zero and increases with increasing error. Some candidates for $f$ are the mean deviation $$f(\epsilon_i^{(j)}) = \frac{1}{N}\sum_{i=0}^{N-1}|\epsilon_i^{(j)}| \tag{9}$$

and the auto-correlation $$f(\epsilon_i^{(j)}) = \sqrt{\left|\frac{1}{N}\sum_{i=k}^{N-1}\epsilon_i^{(j)}\epsilon_{i-k}^{(j)}\right|}, \tag{10}$$

where the "lag" k is an integer constant and any undefined summation terms are assumed to be handled appropriately (e.g., by reflective boundary conditions). (If k=0 then Eq. 10 reduces to the root-mean-square deviation.) It may also be useful to "pre-process" the $\epsilon_i^{(j)}$ before passing them to $f$. Some candidate pre-processing functions are the smoothing filter $$\tilde{\epsilon}_i^{(j)} = \frac{1}{2l+1}\sum_{n=-l}^{l}\epsilon_{i+n}^{(j)}, \tag{11}$$

where the tilde denotes pre-processed results and the undefined summation terms when i+n<0 and i+n≧N are assumed to be handled appropriately (e.g., by reflective boundary conditions), and the "windowing" filter $$\tilde{\epsilon}_i^{(j)} = w_i\epsilon_i^{(j)}, \tag{12}$$

where the $w_i$ are constants which satisfy the symmetry condition $w_i = w_{N-1-i}$.

To complete the inspection algorithm, let $$\epsilon_d = f_d(\epsilon^{(0)}, \epsilon^{(1)}, \epsilon^{(2)}, \epsilon^{(3)}) \tag{13}$$

and $$\epsilon_s = f_s(\epsilon^{(0)}, \epsilon^{(1)}, \epsilon^{(2)}, \epsilon^{(3)}) \tag{14}$$

be single-number measures of the overall severity of dip and saddle, respectively. These functions are designed to combine the information from the four independent views to produce severity numbers which are substantially independent of the orientation of the container. (A necessary but not sufficient condition for rotation invariance is for these functions to be invariant under cyclic permutations of their arguments.) For example, when a dip defect is centered in mirror 3 then $\epsilon^{(3)} >> \epsilon^{(0)} \approx \epsilon^{(1)} \approx \epsilon^{(2)} \approx 0$, while if the defect is in between mirrors 2 and 3 then $\epsilon^{(3)} \approx \epsilon^{(2)} >> \epsilon^{(0)} \approx \epsilon^{(1)} \approx 0$. However, $\epsilon_d$ should be the same in both cases.

The results shown in FIGS. 12–15 use the mean-deviation form (Eq. (9)) for $f$, no pre-processing, and the single combined severity measure $$\epsilon = \epsilon^{(0)} + \epsilon^{(1)} + \epsilon^{(2)} + \epsilon^{(3)} \tag{15}$$

for both dip and saddle. Containers are rejected if $\epsilon > \epsilon_t$, where $\epsilon_t$ is a user-defined threshold relating to sealing surface tolerances.

Figure 16:
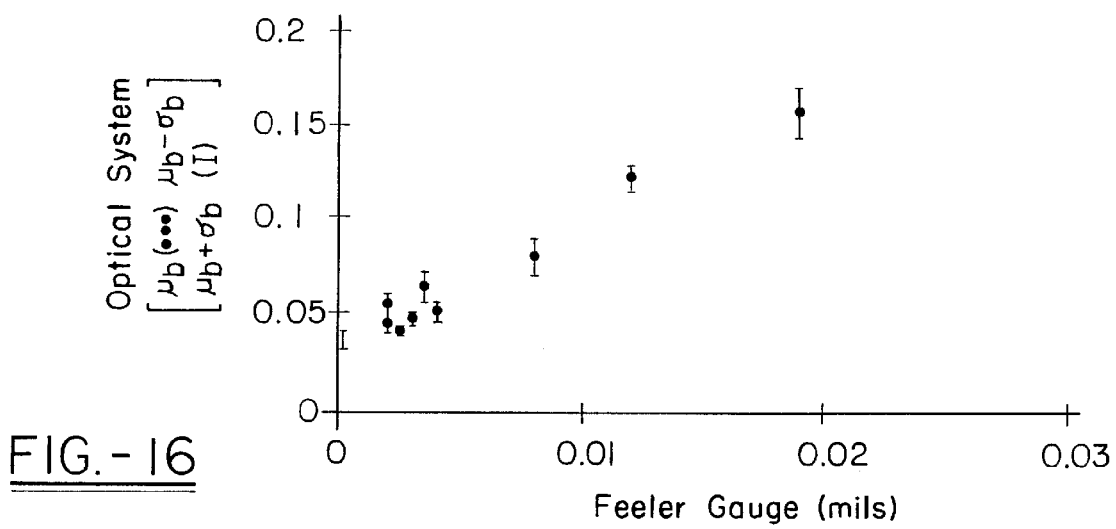
FIG. 16 is a plot of defects detected using the machine vision system according to the invention as compared to measured defects.

Turning to FIG. 16, a plot is shown of measurements from machine vision system 10 for sealing surface 52 of a number of glass containers, and more particularly for commercially available juice bottles. The error bars about each of the measured results show one standard deviation about the measured results. These results are plotted against mechanical measurements of the actual defects in each of the bottles performed by feeler gage measurement with sealing surface 52 positioned on a flat surface. The value of $\epsilon$ (y-axis; scaled in an arbitrary manner) is plotted versus the maximum depth of the dip or saddle defect (x-axis; measured in mils). The results of system 10 show excellent correlation to the mechanical measurements, indicating accurate detection of dip and saddle defects.

For measurement of dip and saddle defects, one aspect of the invention relates to the ability to discern dip and saddle defects by acquiring a complete image of the sealing surface 52 from a shallow view angle created by the illumination system 12 as previously described. The illumination system 12 provides backlighting with respect to the sealing surface 52 to generate an image of the profile from a viewing angle which allows discernment of the dip or saddle defect. The illuminating light generating the profile image is folded via the reflecting mirror systems to effectively position the imaging system or camera optical axis nearly parallel to the plane of the sealing surface 52 or at a shallow viewing angle so that height variations of the sealing surface 52 will become apparent as shown in the figures. By acquiring images for the entire defined finish surface, which in this case is sealing surface 52, the system allows dip and saddle defects to be quickly and accurately determined. Thus, the view angle of the imaging system is preferably from almost horizontal to about 60 degrees, although a range from about 0 degrees to 20 degrees from horizontal is preferred. As the width of the defined finish surface increases, steeper view angles may not accurately determine defects over the entire surface as would be desired. The particular view angle for a given container configuration and particular defined finish surface would be chosen based on the particulars thereof. By backlighting the defined finish surface in this manner, a smooth polynomial curve is imaged which allows extraction of defect information relating to disconformities of the polynomial curve, which can be extracted from the image.

Out of Level Measurements

It is also an aspect of the invention to allow determination of out-of-level sealing surfaces 52 which can result in improper sealing of a container as previously indicated. A machine vision approach to out-of-level gaging has the advantage that the out-of-level angle θ is measured for every container, allowing trends to be detected before they lead to containers which must be rejected. Although out-of-level defects are somewhat similar to the determination of dip or saddle defects associated with sealing surface 52, out-of-level defects relate to a sealing surface 52 which is tilted or skewed instead of having localized dip or saddle defects.

Out-of-level defects are found using a similar optical and imaging system as described with respect to dip and saddle defect measurement above, with the image of the entire sealing surface 52 acquired similarly. Again, imaging of the sealing surface 52 as described will generate an image which in the ideal container would form a smooth polynomial curve of a particular configuration. For out-of-level measurements, a circular sealing surface 52 is imaged by generating a profile or silhouette of the sealing surface 52 from a shallow viewing angle.

When a circle is viewed from an angle $\Theta$ (measured from the normal to the circle), the major and minor radii of the apparent ellipse are related to $\Theta$ by the expression $$\cos\Theta = \frac{r_<}{r_>}. \tag{16}$$

Calibration of the out-of-level gage is performed by imaging a good container (i.e., one whose sealing surface 52 is flat and level) and calculating and storing the calibration angles $$\bar{\theta}^{(j)} = \cos^{-1}\left(\frac{\bar{r}_<^{(j)}}{\bar{r}_>^{(j)}}\right), \tag{17}$$

where $\bar{r}_<^{(j)}$ and $\bar{r}_>^{(j)}$ are the minor and major radii of the best-fit ellipse of view j of the good (calibration) container, and the overbars denote calibration quantities. (If the four-mirror assembly of the preferred embodiment is perfectly machined and aligned, then all four of these angles should be identical. However, in practice, due to mechanical tolerances, they will generally differ slightly, making calibration desirable or necessary for accurate defect determination.)

Consider a Cartesian coordinate system with its origin at the center of the calibration sealing surface and defined by the unit vectors $\hat{e}_1$, $\hat{e}_2$, $\hat{e}_3$, where $\hat{e}_3$ is normal to the calibration sealing surface. Then $$\hat{n}^{(j)} = \hat{e}_1 \sin\bar{\theta}^{(j)} \cos\bar{\phi}^{(j)} + \hat{e}_2 \sin\bar{\theta}^{(j)} \sin\bar{\phi}^{(j)} + \hat{e}_3 \cos\bar{\theta}^{(j)} \tag{18}$$

is a unit vector along the direction of view j, where $\bar{\theta}^{(j)}$ is the polar angle (i.e., the angle measured from $\hat{e}hd 3$) and $\bar{\phi}^{(j)}$ the azimuthal angle (i.e., the angle in the $\hat{e}_1$, $\hat{e}_2$ plane measured from $\hat{e}_1$ towards $\hat{e}_2$) of view j, given by $$\bar{\phi}^{(j)} = \frac{\pi}{2}j, \tag{19}$$

where $\bar{\phi}^{(j)}$ is an ideal value which does not consider machining or alignment tolerances for the reflecting mirror assembly. This value may also be derived from calibration to avoid any possible errors if desired. Then letting $$\hat{n} = \hat{e}_1 \sin\theta \cos\phi + \hat{e}_2 \sin\theta \sin\phi + \hat{e}_3 \cos\theta \tag{20}$$

be the unit vector normal to the sealing surface 52 of a container under inspection, where $\theta$ and $\phi$ are the polar and azimuthal angles, respectively, the dot product $\hat{n} \cdot \hat{n}^{(j)}$ is the cosine of the angle between the normal of the sealing surface 52 and the view direction j. Hence, from Eq. (14) it is concluded that $$\hat{n} \cdot \hat{n}^{(j)} = \frac{r_<^{(j)}}{r_>^{(j)}}. \tag{21}$$

Combining Eqs. (16), (18) and (19) gives $$\frac{r_<^{(j)}}{r_>^{(j)}} = \sin\theta\cos\phi\sin\bar{\theta}^{(j)}\cos\bar{\phi}^{(j)} + \sin\theta\sin\phi\sin\bar{\theta}^{(j)}\sin\bar{\phi}^{(j)} + \cos\theta\cos\bar{\theta}^{(j)}. \tag{22}$$

Since $\bar{\theta}^{(j)}$ and $\bar{\phi}^{(j)}$ are known from calibration and $r_<^{(j)}$ and $r_>^{(j)}$ are known for every inspected container from the best-fit ellipse procedure these four equations (j=0,1,2,3) can be solved for the two unknowns $\theta$ and $\phi$. If we assume $\theta$ is small (the container out-of-level angle is typically only a few degrees), then we can make the approximations $\cos\theta \approx 1$ and $\sin\theta \approx \theta$. Combining Eqs. (20) with Eqs. (17) and making these approximations gives $$\theta \approx \sqrt{\frac{u_0^2 + u_1^2 + u_2^2 + u_3^2}{2}}, \tag{23}$$

where $$u_j = \frac{1}{\sin\bar{\theta}^{(j)}}\left(\frac{r_<^{(j)}}{r_>^{(j)}} - \cos\bar{\theta}^{(j)}\right) \tag{24}$$

and $\theta$ is in radians. It should be noted that $\theta$ is only well-defined if the container sealing surface 52 is substantially flat, even though tilted. Therefore, the dip and saddle inspection is preferably performed prior to the out-of-level inspection, and if the container sealing surface 52 is found to be substantially flat, the out-of-level inspection results can be considered accurate.

Height Measurements

The method and apparatus of the invention also allow for height measurements of a container, corresponding to the upper level of the sealing surface 52 to be monitored and evaluated for conformance to predetermined height tolerances for a container. A machine vision approach to height gaging has the advantage that the height deviation $\Delta h$ is measured for every container, allowing trends to be detected before they lead to containers which must be rejected. Again, in order to ensure accuracy of measurement, it may be desirable to calibrate the instrument to a particular container configuration having a predetermined height. During a similar calibration to that done for out-of-level gaging, the coordinates $\bar{X}_c^{(j)}$, $\bar{Y}_c^{(j)}$ of the center of the best-fit ellipse of each view (j=0,1,2,3) from the reflecting mirror assembly are calculated and stored. Also, a mean value of the radius of the calibration sealing surface 52 as it appears in the dip-saddle image (and expressed in pixels) is estimated as $$\bar{r} = \tfrac{1}{4}(\bar{r}_>^{(0)} + \bar{r}_>^{(1)} + \bar{r}_>^{(2)} + \bar{r}_>^{(3)}). \tag{25}$$

If we shift the calibration container up a distance $\Delta h$, then the new centers $(X_c^{(j)}, Y_c^{(j)})$ of the best-fit ellipses shift in a predictable fashion based on the imaging geometry. A careful analysis of the geometry gives $$\Delta h = \frac{\Delta w^{(j)}}{\sin \overline{\theta}^{(j)}}, \quad (26)$$

where $$\Delta w^{(0)} = X_c^{(0)} - \tilde{X}_c^{(0)},$$

$$\Delta w^{(1)} = -(Y_c^{(1)} - \tilde{Y}_c^{(1)}),$$

$$\Delta w^{(2)} = -(X_c^{(2)} - \tilde{X}_c^{(2)}),$$

$$\Delta w^{(3)} = Y_c^{(3)} - \tilde{Y}_c^{(3)} \quad (27)$$

During inspection, the axes of the containers may randomly shift slightly away from the system optical axis, and these lateral shifts will cause apparent height shifts for any given view j even if the containers all have exactly the same height. However, if one averages the $\Delta h$ values computed from all views from the optical system, the effects of lateral shifts substantially cancel out, and an accurate measure of the height shift is obtained. Thus, $$\Delta h = \frac{1}{4} \sum_{j=0}^{3} \left( \frac{\Delta w^{(j)}}{\sin \overline{\theta}^{(j)}} \right) \quad (28)$$

is an estimate (in pixels) of the difference in height between an inspected container and the calibration container. The ratio $\Delta h / \overline{r}$ gives the height difference as a fraction of the radius of the container. Similar to the out-of-level measurement, any height measurement $\Delta h$ is only well-defined if the container sealing surface 52 is substantially flat and level. The dip and saddle and out-of-level inspections should be performed prior to the height inspection, and if the container is found to be substantially flat and level, the height inspection will be accurate.

Container Opening Inspection

Figure 17:
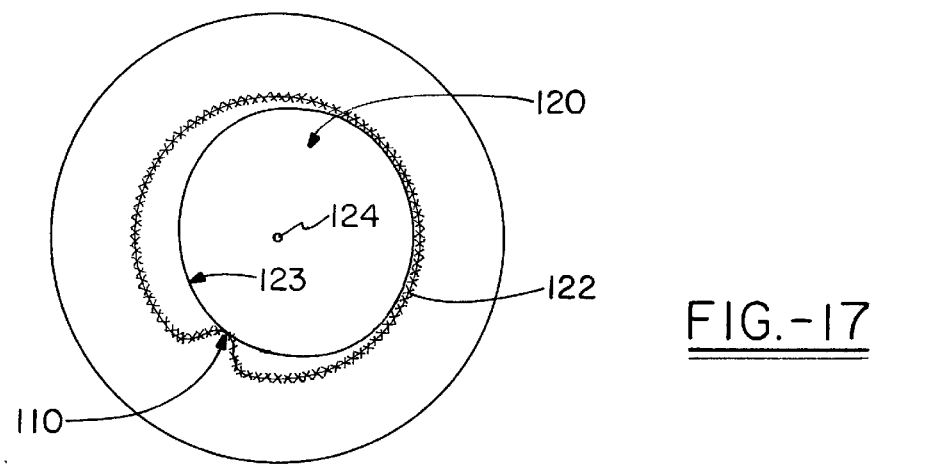
FIG. 17 is an image of a container defined finish surface for detection of other defects associated with the defined finish surface.

It is also desirable to monitor the size of the container opening and particularly of the inside diameter of the container opening or possibly of the neck of a container ending in the opening. Thus, a defined finish surface in accordance with the invention may be any of the plurality of inside diameters associated with the container opening or neck region, which must be within predefined tolerances to allow proper filling of the containers. It is also an aspect of the invention that stuck-glass defects associated with the container opening or neck region be detected to ensure that such containers are rejected prior to filling to avoid possible contamination by glass fragments. In the invention, the container opening inspection may be performed using edge finding techniques as previously described with respect to dip and saddle defect detection, but instead used to outline the container bore. Referring to FIG. 17, container opening inspection and stuck-glass inspection will be described with respect to a container opening generally designated 120. This figure is similar to FIG. 9, with the image allowing bore tolerances to be inspected along with defects such as stuck-glass defects as shown at 110. Similar to previously described FIG. 11, white crosses 122 have been added to the image corresponding to the edges of the bore 120 as detected by the processing system 90. Edge finding by the processing system 90 may be performed by scanning outward from the center of the image along a number of equally-spaced radial lines. The number of radial lines along which edge detection is performed may be specified to allow desired resolution for a particular application, and the results shown in the FIGS. use 120 scans. Along each of the radial lines from center point 124, the edge is located by noting the position of the first significant light-to-dark transition. The set of coordinates of the edge points found defines the locus of the bore outline. Once the bore outline is extracted from the image, the image is no longer needed and may be discarded, and again the graphics as shown in FIG. 17 are for illustrative purposes only, and even the image may not need to be displayed. It is noted within the bore of container opening 120, the stuck-glass defect 110 results in a disconformity in the circular opening 120 which may be detected. To enhance the light-to-dark transitions at the edge of the container bore, an illuminating light may be positioned beneath the container so as to direct illuminating light through the container along the axis of the opening 120, in a backlit arrangement. Such an approach requires that the container be transparent or translucent to allow illuminating light to pass through in this manner. Other illuminating techniques may provide light reflection through the opening 120 to accomplish a similar objective. Further, if the containers to be inspected are transported on an opaque conveyor belt or system, and a backlighting illumination system is used, the containers can be moved onto a so-called "dead plate", comprising a stationary smooth surface over which the containers are pushed by pressure from subsequent bottles. The dead plate can be made of a translucent diffusing material and backlighted to provide diffused backlighting for inspection of bore diameters and stuck-glass defects. Alternatively, the containers may be transferred from a conveyor system to a so-called "side-grip conveyor", comprising two parallel vertical belts moving synchronously and separated by about the diameter of the container body. The side-grip conveyor suspends the containers in midair during transport to allow illuminating light to be positioned beneath the containers appropriately. Given the set of N points $x_i$, $y_i$ ($0 \leq i > N$) corresponding to a measured bore outline, the center of the bore is estimated as the centroid $$X_c = \frac{1}{N} \sum_{i=0}^{N-1} x_i, \quad (29)$$

$$Y_c = \frac{1}{N} \sum_{i=0}^{N-1} y_i.$$

The point $X_c$, $Y_c$ is shown in FIG. 17 at 124. Then calculate the "polar coordinates" $r_i$, $\theta_i$ which satisfy $$x_i = X_c + r_i \cos \theta_i,$$

$$y_i = Y_c + r_i \sin \theta_i. \quad (30)$$

Figure 18:
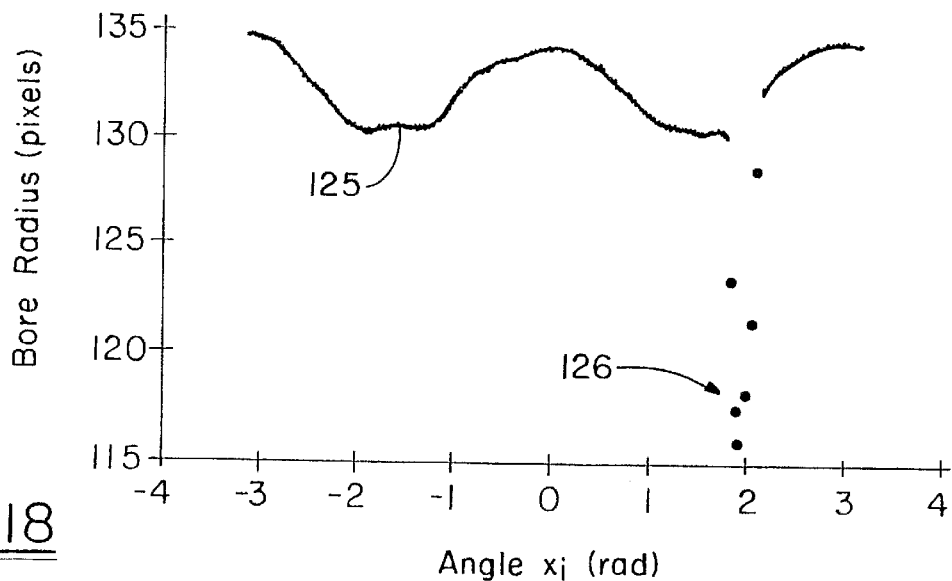
FIGS. 18–19 are graphical representations of image information for the defined finish surface as shown in FIG. 17.

The points $r_i$, $\theta_i$ are plotted in FIG. 18 for the container opening. An ideal container would yield a horizontal line at a constant bore radius. The actual results show an undulating smooth curve 125 interrupted by a sharp spike at 126. Curve 125 has two weak maxima and two weak minima, indicating that the container bore is slightly elliptical. Spike 126 corresponds to stuck-glass defect 110. After finding the bore outline at 122, the largest circle 123 which can be inscribed within the bore is determined, and used to characterize the effective (i.e., useful) bore size. The largest inscribed circle simulates the operation of a mechanical plug gage, in the sense that a container will move around slightly to allow the plug gage plunger to slide into the bore.

Figure 19:
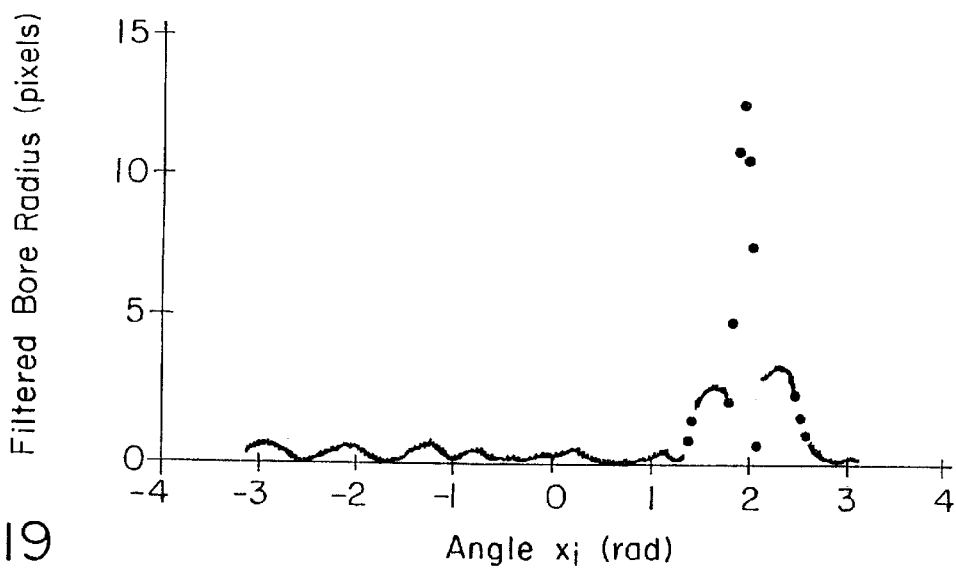

For stuck-glass detection, spikes such as 126 must be detected while the smooth undulations of curve 125 should not be misconstrued as such defects. An effective approach is to apply a high-pass filter to the data represented in the curve of FIG. 18, which reduces low-frequency undulations while preserving high-frequency spikes. The mathematics of filtering is well-known, and there are many high-pass filter designs. A simple and effective filter is $$\hat{r}_i = \left| r_i - \frac{1}{2K+1} \sum_{k=-K}^{K} r_{i+k} \right|, \tag{29}$$

where K is a constant which determines the cut-on frequency of the filter (small values of K correspond to high cut-on frequencies), the hat denotes the filtered result, the absolute value forces the stuck-glass spikes to be positive, and cyclic boundary conditions are assumed when i+k<0 or i+k≧N. The result of applying the filter of Eq. (29) with K=10 to the curve of FIG. 18 is shown in FIG. 19. The curve is now substantially zero except in the vicinity of the stuck-glass spike. Note that the 5 pixel peak-to-peak ripple of curve 125 has now been substantially reduced, while the amplitude of the stuck-glass spike is only slightly reduced. Hence, the filtering has improved the "signal-to-noise ratio" for stuck-glass detection. A container may then be rejected for a stuck-glass defect if max($\hat{r}_i$)>t where t is a user-defined rejection threshold. By adjusting K and t the user can adjust the sensitivity of the inspection to stuck-glass defects.

In practice, calculation of the largest inscribed circle 123 from the bore outline must be done quickly for desired inspection speeds such as 800 containers per minute. To accommodate such processing speeds, the calculation is performed in tens of milliseconds, or faster. Algorithms suitable for accomplishing this goal are known, for example as specified in "A sweepline algorithm for Voronoi diagrams" by Steve Fortune, Algorithmica, Vol. 2, pp. 153–174, 1987; see also "The Algorithm Design Manual" by Steven Skiena, Springer-Verlag, pp. 358–360, 1997).

The methods and apparatus of the invention provide an effective and adaptable system which allows various containers to be inspected in an in-line process for various particular requirements as desired. A plurality of inspections can be performed simultaneously and at much greater speeds than mechanical or other optical systems. Although preferred embodiments of the present invention have been described herein, various modifications or changes are contemplated within the scope of the invention. The invention is therefore not restricted to that described above and shown in the drawings but may be modified within the scope of the appended claims.

What is claimed is:

1. The process of inspecting a container comprising the steps of:
   a) positioning a container to be inspected at a predetermined location relative to an optical inspection system;
   b) illuminating at least a portion of said container over at least one defined finish surface of said container;
   c) capturing illuminating light from an area corresponding to at least said one defined finish surface without manipulation of said container, and
   d) determining from information analyzed in said captured illuminating light if said at least one defined finish surface of said container is within predetermined tolerances.

2. The process of claim 1, wherein said at least one defined finish surface is the sealing surface about an opening of said container.

3. The process of claim 1, wherein said at least one defined finish surface is the exterior of a thread associated with an opening of said container.

4. The process of claim 1, wherein said at least one defined finish surface is an inside diameter of a neck of an opening of said container.

5. The process of claim 1, wherein said at least two defined finish surfaces are illuminated in step b) and illuminating light is captured from said at least two defined finish surfaces in step c), wherein each of said at least two defined finish surfaces is determined to be within the predetermined tolerances in step d).

6. The process of claim 2, wherein said step of determining if said sealing surface is within predetermined tolerances includes determination of whether said sealing surface has a defect from the group of defects consisting of dip defects, saddle defects, out-of-level defects and height defects.

7. The process of claim 1, wherein said step of determining if said defined finish surface is within predetermined tolerances includes determination of whether said surface has a defect from the group of defects consisting of dip defects, saddle defects, out-of-level defects, height defects, diameter defects, stuck glass defects, wall thickness defects or thread defects.

8. The process of claim 1, wherein said illumination of said at least one defined finish surface comprises backlighting said defined finish surface with an illumination source to create a silhouette of said defined finish surface in said captured illuminating light.

9. The process of claim 1, wherein said step of capturing illuminating light includes reflecting at least a portion of said illuminating light from a first optical axis to at least a second optical axis for detection by a light sensing device.

10. The process of claim 1, wherein at least two defined finish surfaces are illuminated in step b).

11. The process of claim 10, wherein said at least two defined finish surfaces correspond to a sealing surface of said container and an inside diameter of an opening in said container.

12. The process of claim 10, wherein said at least two defined finish surfaces correspond to an inside surface of a wall of said container, and an outside surface of said wall, wherein said step of determining if said container is within predetermined tolerances includes determination of the container wall thickness between said at least two defined finish surfaces.

13. The process of claim 1, wherein said step of determining if said defined finish surface is within predetermined tolerances includes selectively applying a high pass filter to said information captured in said illuminating light to provide filtered data, and determining from said filtered data whether said surface has a defect.

14. The process of inspecting a container comprising the steps of:
   a) positioning of a container to be inspected at a predetermined location relative to an optical inspection system;
   b) directing illuminating light from a predetermined viewing angle toward a sealing surface associated with an opening of said container;
   c) reflecting illuminating light passing over said sealing surface along an optical axis;
   d) capturing illuminating light along said optical axis, and
   e) determining if said sealing surface of said container is within predetermined tolerances.

15. The process according to claim 14, wherein said predetermined viewing angle along which illuminating light is directed is between substantially 0 degrees and 60 degrees from horizontal.

16. The process according to claim 14, wherein said viewing angle is between substantially 0 degrees and 20 degrees from horizontal.

17. The process according to claim 14, wherein illuminating light is directed toward the entire sealing surface such that information relating to the entire sealing surface is captured simultaneously.

18. The process according to claim 14, wherein said step of determining if said sealing surface is within predetermined tolerances includes determination of whether dip defects are present in said sealing surface.

19. The process according to claim 14, wherein said step of determining if said sealing surface is within predetermined tolerances includes determination of whether saddle defects are present in said sealing surface.

20. The process according to claim 14, wherein said step of determining if said sealing surface is within predetermined tolerances includes determination of whether out-of-level defects are present in said sealing surface.

21. The process according to claim 14, wherein said step of capturing illuminating light includes directing illuminating light passing over said sealing surface to a video imaging system which captures an image of said sealing surface for analysis.

22. The process according to claim 14, wherein said step of capturing illuminating light comprises positioning a plurality of reflecting surfaces at an angle with respect to said sealing surface so as to reflect light rays passing over said sealing surface to a light sensing device.

23. The process according to claim 22, wherein said plurality of reflecting surfaces comprise four mirrors positioned relative to said sealing surface, each of said mirrors reflecting light rays passing over a predetermined portion of said sealing surface, and together reflecting light rays passing over the entire sealing surface.

24. A process of inspecting a container sealing surface to determine whether such surface is within predetermined tolerances, comprising the steps of:
   a) positioning a container to be inspected at a predetermined location relative to an optical inspection system;
   b) illuminating at least a portion of said container over at least the sealing surface of said container;
   c) acquiring an image of said sealing surface from illuminating light passing over said sealing surface;
   d) detecting in said image the edge of said sealing surface;
   e) determining if a predetermined polynomial curve can be modelled to said detected edge, and rejecting said container if not or calculating the parameters of said polynomial curve and continuing with process step f);
   f) determine using at least said parameters of said polynomial curve whether said sealing surface is within predetermined tolerances and rejecting said container if not.

25. The process of claim 24, wherein said step f) comprises determining errors between said polynomial curve and said edge of said sealing surface, and determining whether said errors are within said predetermined tolerances.

26. The process of claim 24, wherein said step f) comprises determining the out-of-level angle of said sealing surface, and determining whether said out-of-level angle is within said predetermined tolerances.

27. The process of claim 24, wherein said step f) comprises determining the height shift of said sealing surface, and determining whether said height shift is within said predetermined tolerances.

28. The process of claim 24, wherein said step of illuminating said sealing surface of said container comprises positioning at least one source of illuminating light at a predetermined viewing angle relative to said sealing surface.

29. The process of claim 28, wherein said predetermined viewing angle is from about zero degrees to about sixty degrees from a horizontal plane including at least a portion of said sealing surface.

30. An apparatus for inspection of a container comprising a source of illuminating light to direct light over at least one defined finish surface of a container, a light sensor to capture light from an area corresponding to at least said one defined finished surface without manipulation of said container, and to provide image information relating to said at least one defined finish surface, and a processor using said image information to determine if said at least one defined surface is within predetermined tolerances.

31. The apparatus according to claim 30, wherein,
   said source of illuminating light comprises a plurality of illumination sources positioned at predetermined locations about a defined finish surface to be inspected, to direct illuminating light over the entire defined finish surface.

32. The apparatus according to claim 30, further comprising an optical assembly including a plurality of reflecting surfaces mounted within a housing, said reflecting surfaces disposed at a predetermined angle so as to capture and reflect light from said source of illuminating light which passes over said defined finish surface to said light sensor.

33. The apparatus according to claim 32, wherein the position of said optical assembly is adjustable relative to said source of illuminating light.

34. The apparatus according to claim 30, wherein said light sensor is an imaging system which will capture a silhouetted image of said defined finish surface and generate image information which is supplied to said processor for analysis.

35. The apparatus according to claim 30, further comprising a first optical system including a first light sensor to capture light from a first defined finish surface, and a second optical system including a second light sensor to capture light from a second defined finish surface, wherein said processor then determines if both of said first and second defined finish surfaces are within predetermined tolerances.

36. The apparatus according to claim 35, wherein said first optical system comprises at least one reflecting surface to capture illuminating light directed at a predetermined viewing angle over a sealing surface as said defined finish surface, said reflecting surface directing said illuminating light to said first light sensor to generate image information corresponding to a silhouette of said sealing surface for analysis.

37. The apparatus according to claim 35, wherein said second optical system comprises an optical lens to focus light passing over said second defined finish surface onto a light sensor to form an image of said second defined finish surface which will allow dimensional characteristics of said second defined finish surface to be analyzed by said processor.

38. The apparatus according to claim 30, wherein said at least one defined finish surface is the sealing surface of said container, and said light sensor is a single camera apparatus to capture light passing over said sealing surface, wherein said light passing over said sealing surface is reflected by a plurality of mirrors and directed at a focussing lens of said camera.

39. The apparatus according to claim 30, wherein said source of illuminating light directs light over at least two of said defined finish surfaces, and said light sensor comprises at least two camera devices, each of which provides image information from one of said at least two defined finish surfaces so as to simultaneously determine if each of said at least two defined finish surfaces is within predetermined tolerances.

40. The apparatus according to claim 30, wherein said processor includes a high pass filtering system which is selectively applied to said image information to detect abnormalities in said image information.

41. The apparatus according to claim 30, wherein said at least one defined finish surface is the sealing surface of said container and further comprising at least four mirrors positioned relative to said sealing surface, each of said mirrors reflecting light rays passing over a predetermined portion of said sealing surface, and together reflecting light rays passing over the entire sealing surface to said light sensor.

42. The process of inspecting a container opening comprising the steps of:
   a) positioning of a container to be inspected at a predetermined location relative to an optical inspection system;
   b) directing illuminating light so as to illuminate the container opening and at least one defined finish surface corresponding to at least one inside surface associated with said container opening;
   c) directing light from the area of said at least one defined finish surface along an optical axis;
   d) capturing illuminating light along said optical axis, and
   e) determining if said at least one defined finish surface is within predetermined tolerances.

43. The process according to claim 42, wherein said predetermined tolerances correspond to acceptable dimensions of said container opening.

44. The process according to claim 42, wherein said predetermined tolerances correspond to the presence of stuck glass in the region of said container opening.

45. A machine vision system for inspection of a container comprising:
   a source of illuminating light to direct light over at least one defined finish surface of a container;
   a light sensor to capture light from an area corresponding to at least one defined finish surface, and to provide image information relating to said at least one defined surface,
   a processor using said image information to determine if said at least one defined surface is within predetermined tolerances; and
   a user interface coupled to said processor to control operation of said machine vision system and to select configuration of various components of said systems to inspect said container for defects selected from the group consisting of dip-saddle defects, container out-of-level defects, plug defects, incorrect height dimensions, incorrect wall thickness dimensions, internal crack defects, stuck glass defects, and thread defects.

46. The machine vision system according to claim 45, wherein said user interface is a touch screen interface.

47. The machine vision system according to claim 45, wherein said source of illuminating light comprises a plurality of illuminating sources and said user interface is used to select at least one of said plurality of illuminating sources to direct illuminating light over said defined finish surface.

48. The machine vision system according to claim 45, wherein said user interface is used to strobe the illuminating light source to image said surface.

49. The machine vision system according to claim 45, further comprising a first optical system including a first light sensor to capture light from a first defined finish surface, and a second optical system including a second light sensor to capture light from a second defined finish surface.

50. The machine vision system according to claim 49, wherein said user interface is used to select whether said first optical system or said second optical system or both optical systems are used during said inspection.

51. The machine vision system according to claim 45, wherein said processor comprises at least one algorithm utilizing said image information to quantitatively analyze dimensional characteristics of said container.

* * * * *